United States Patent [19]

Eberbach

[11] Patent Number: 5,366,460
[45] Date of Patent: Nov. 22, 1994

[54] APPARATUS AND METHOD FOR LAPAROSCOPE HERNIA REPAIR

[75] Inventor: Mark A. Eberbach, Tampa, Fla.

[73] Assignee: Cook Incorporated, Bloomington, Ind.

[21] Appl. No.: 934,776

[22] Filed: Aug. 24, 1992

Related U.S. Application Data

[63] Continuation-in-part of Ser. No. 595,956, Oct. 11, 1990, Pat. No. 5,141,515.

[51] Int. Cl.5 ............................................. A61B 19/00
[52] U.S. Cl. ...................................... 606/151; 606/1; 128/898; 128/887
[58] Field of Search .................. 606/1, 108, 110, 113, 606/127, 151, 200, 213; 623/11, 66; 128/887, 898; 604/11–15; 600/37

[56] References Cited

U.S. PATENT DOCUMENTS

| | | | |
|---|---|---|---|
| 460,940 | 10/1891 | Baugh | 606/106 |
| 736,744 | 8/1903 | Kratzmueller | 606/113 |
| 1,225,771 | 5/1917 | Clare | 606/113 |
| 1,275,520 | 8/1918 | Bell . | |
| 1,456,828 | 5/1923 | Pistor | 604/13 |
| 1,711,294 | 4/1929 | Weitzner | 128/887 |
| 3,102,541 | 9/1963 | Adams | 604/15 |
| 3,152,466 | 10/1964 | Williams . | |
| 3,181,533 | 5/1965 | Heath | 606/113 |
| 3,706,311 | 12/1972 | Kokx . | |
| 3,814,095 | 6/1974 | Lubens . | |
| 3,857,395 | 12/1974 | Johnson et al. | 604/14 |
| 3,874,388 | 4/1975 | King et al. | 606/213 |
| 3,918,452 | 11/1975 | Cornfield | 604/11 |
| 4,007,743 | 2/1977 | Blake | 623/11 |
| 4,185,631 | 1/1980 | McConnell | 604/14 |
| 4,347,847 | 9/1982 | Usher | 606/151 |
| 4,519,643 | 5/1983 | Harris . | |
| 4,557,255 | 12/1985 | Goodman | 128/7 |
| 4,610,659 | 9/1986 | Friese | 604/11 |
| 4,744,364 | 5/1988 | Kensey | 606/213 |
| 4,769,038 | 9/1988 | Bendavid et al. | 606/151 |
| 4,779,616 | 10/1988 | Johnson . | |
| 4,821,741 | 4/1989 | Mohajer | 128/837 |
| 4,854,316 | 8/1989 | Davis | 623/12 |
| 4,873,978 | 10/1989 | Ginsburg . | |
| 4,900,303 | 2/1990 | Lemelson | 606/213 |
| 4,909,789 | 3/1990 | Taguchi | 604/107 |
| 4,964,417 | 10/1990 | Peters | 128/887 |
| 4,981,465 | 1/1991 | Ballan et al. | 128/887 |
| 5,021,059 | 6/1991 | Kensey et al. | 606/213 |
| 5,061,274 | 10/1991 | Kensey | 606/213 |
| 5,108,420 | 4/1992 | Marks | 606/213 |
| 5,116,357 | 5/1992 | Eberbach | 606/213 |
| 5,122,155 | 6/1992 | Eberbach | 606/213 |
| 5,141,515 | 8/1992 | Eberbach | 606/213 |
| 5,147,374 | 9/1992 | Fernandez | 606/151 |
| 5,171,259 | 12/1992 | Inoue | 606/213 |
| 5,192,301 | 3/1993 | Kamiya et al. | 606/213 |

FOREIGN PATENT DOCUMENTS

| | | |
|---|---|---|
| 0362113 | 4/1990 | European Pat. Off. . |
| 2822603 | 11/1979 | Germany . |
| 53-94481 | 8/1978 | Japan . |
| 8911301 | 11/1989 | WIPO . |

OTHER PUBLICATIONS

Francis Stock, "Repair of Large Hernia with Nylon Mesh", Feb. 20, 1954, The Lancet, vol. CCLXVI #6808, p. 395.
Toy Smoot Laparoscopic Hernioplasty–Frederick Toy, Ray Smoot, pp. 151-155-vol. 1, No. 3, 1991, Surgical Laparascopy and Endoscopy Primary Examiner—Stephen C. Pellegrino
Assistant Examiner—Glenn Dawson
Attorney, Agent, or Firm—Richard J. Godlewski

[57] ABSTRACT

Apparatus and method for laparoscopic hernia repair including the use of an introducer sheath housed around an inner tubular plunger. The plunger houses an elongated ribbon formed into a loop, the loop being formed by a bipartite distal end of the ribbon. A patch with a passageway is attached to the loop with each of the two ends of the bipartite distal end of the ribbon being introducible into one end of the passageway for opening the patch into a planar configuration once it is pushed out of the sheath by the plunger.

21 Claims, 20 Drawing Sheets

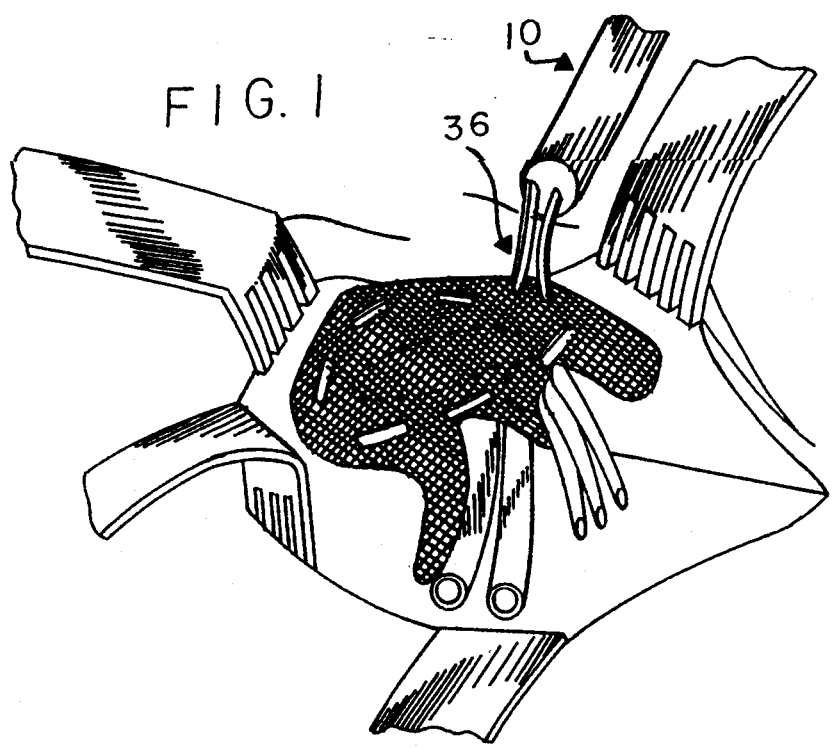
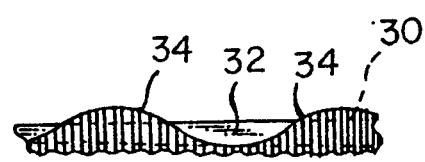
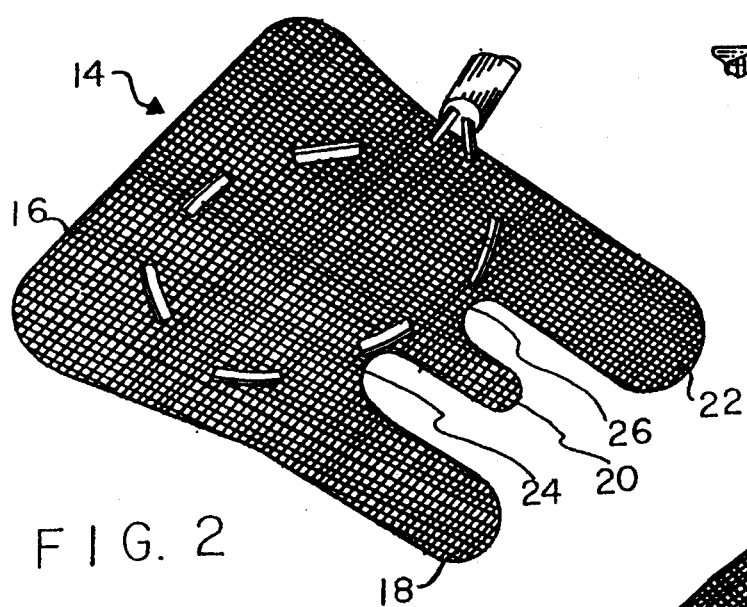
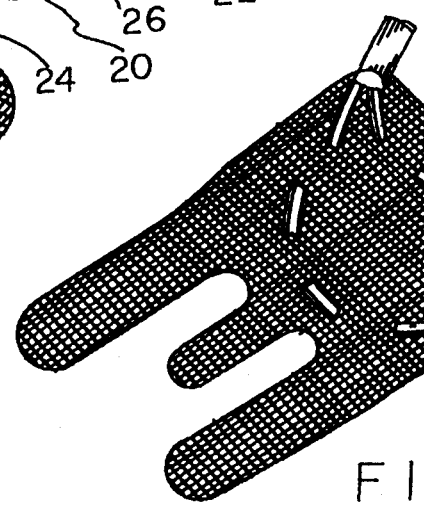

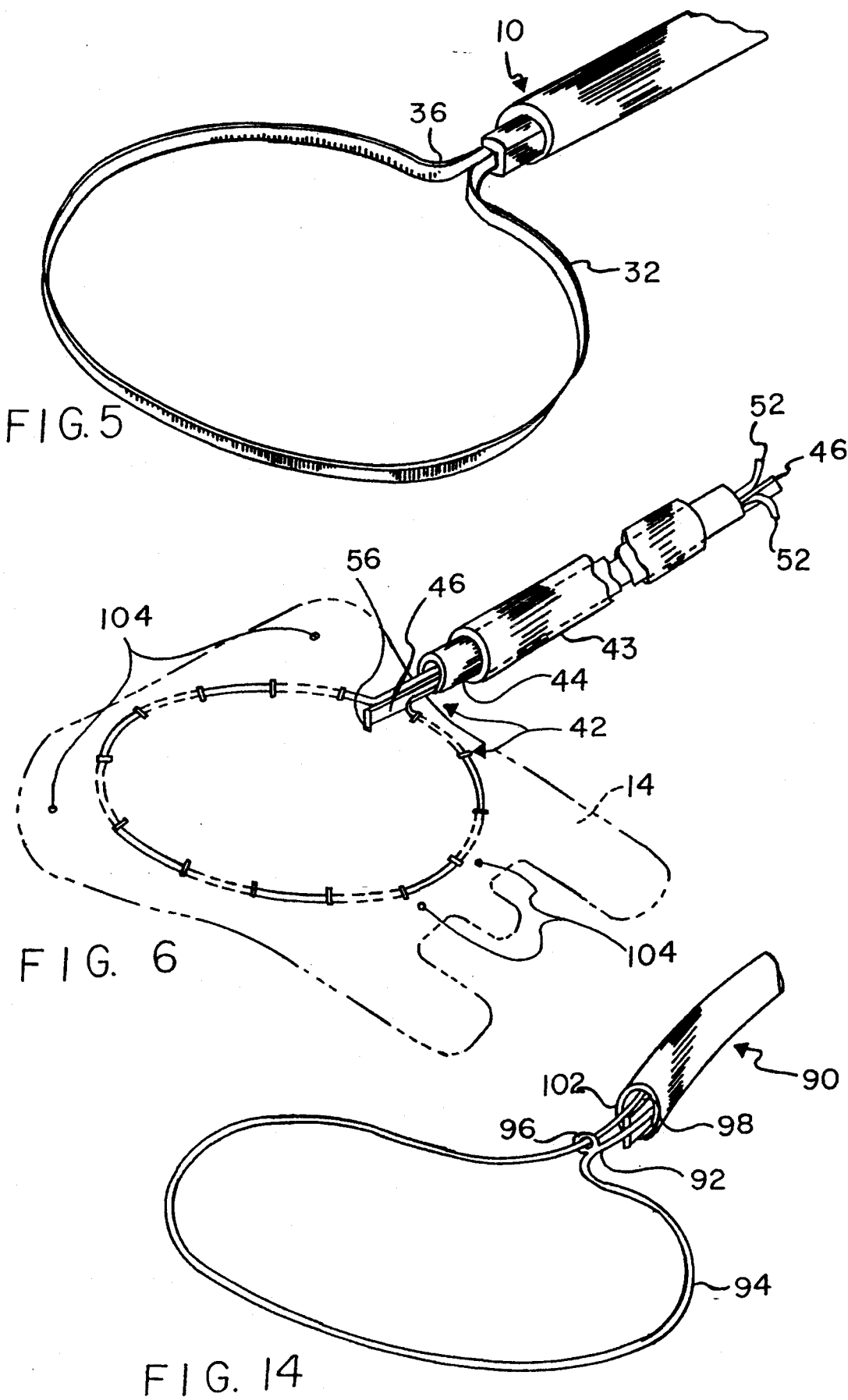

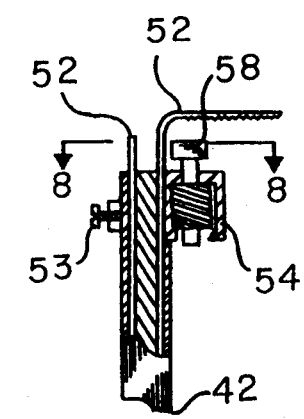
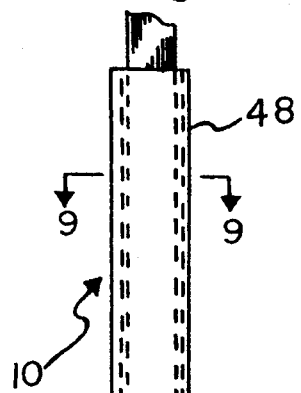
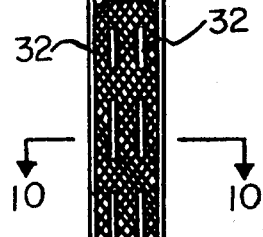
FIG. 7
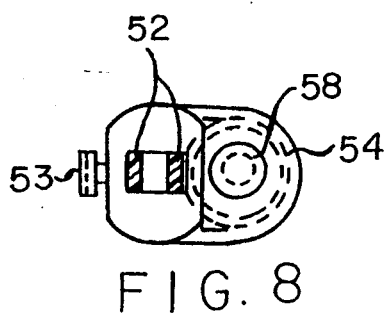
FIG. 8
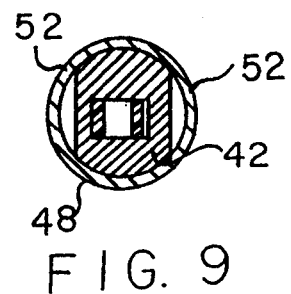
FIG. 9
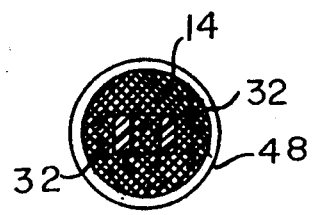
FIG. 10
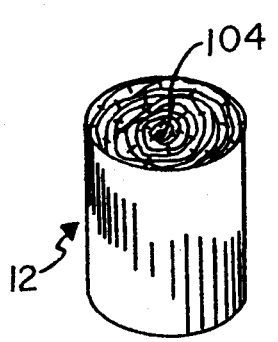
FIG. 15
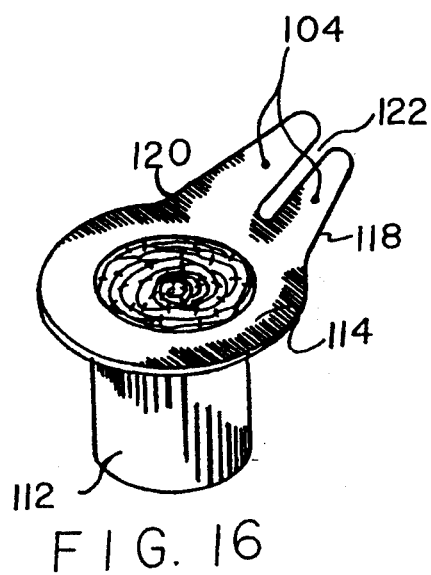
FIG. 16

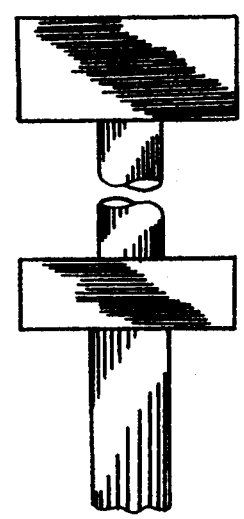
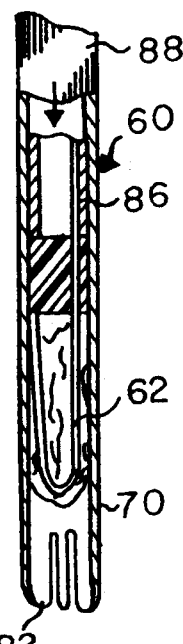
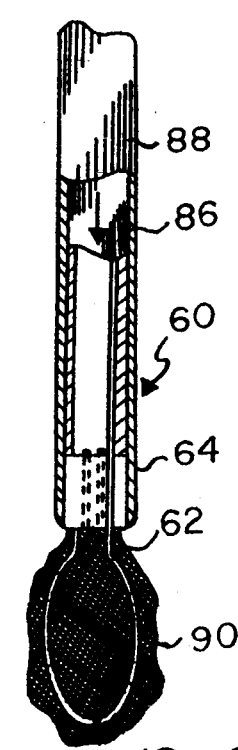
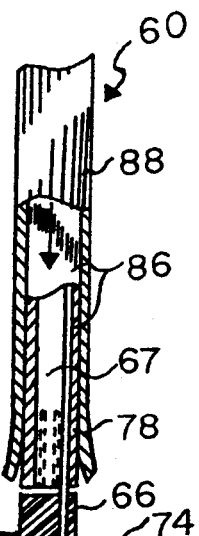
FIG. 11  FIG. 12
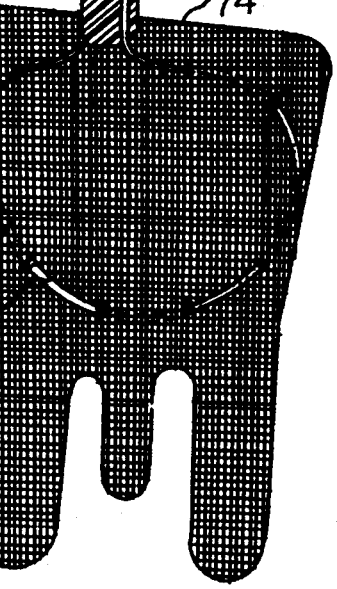
FIG. 13
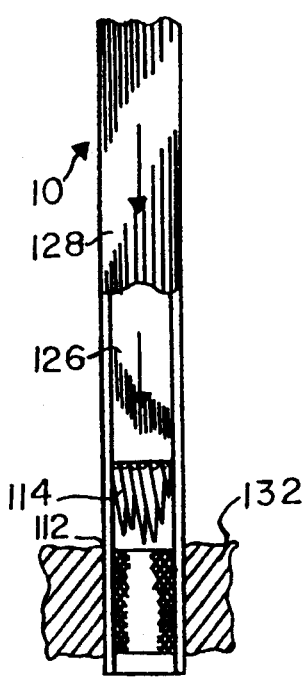
FIG. 17
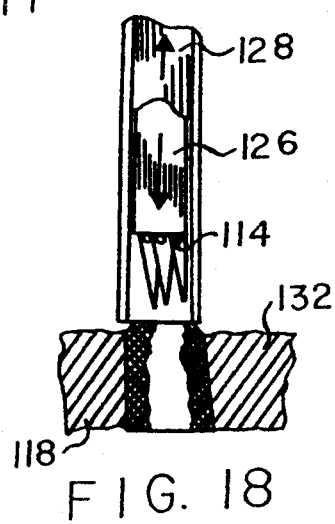
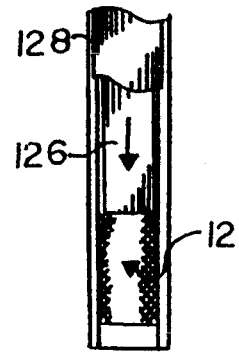
FIG. 18  FIG. 19

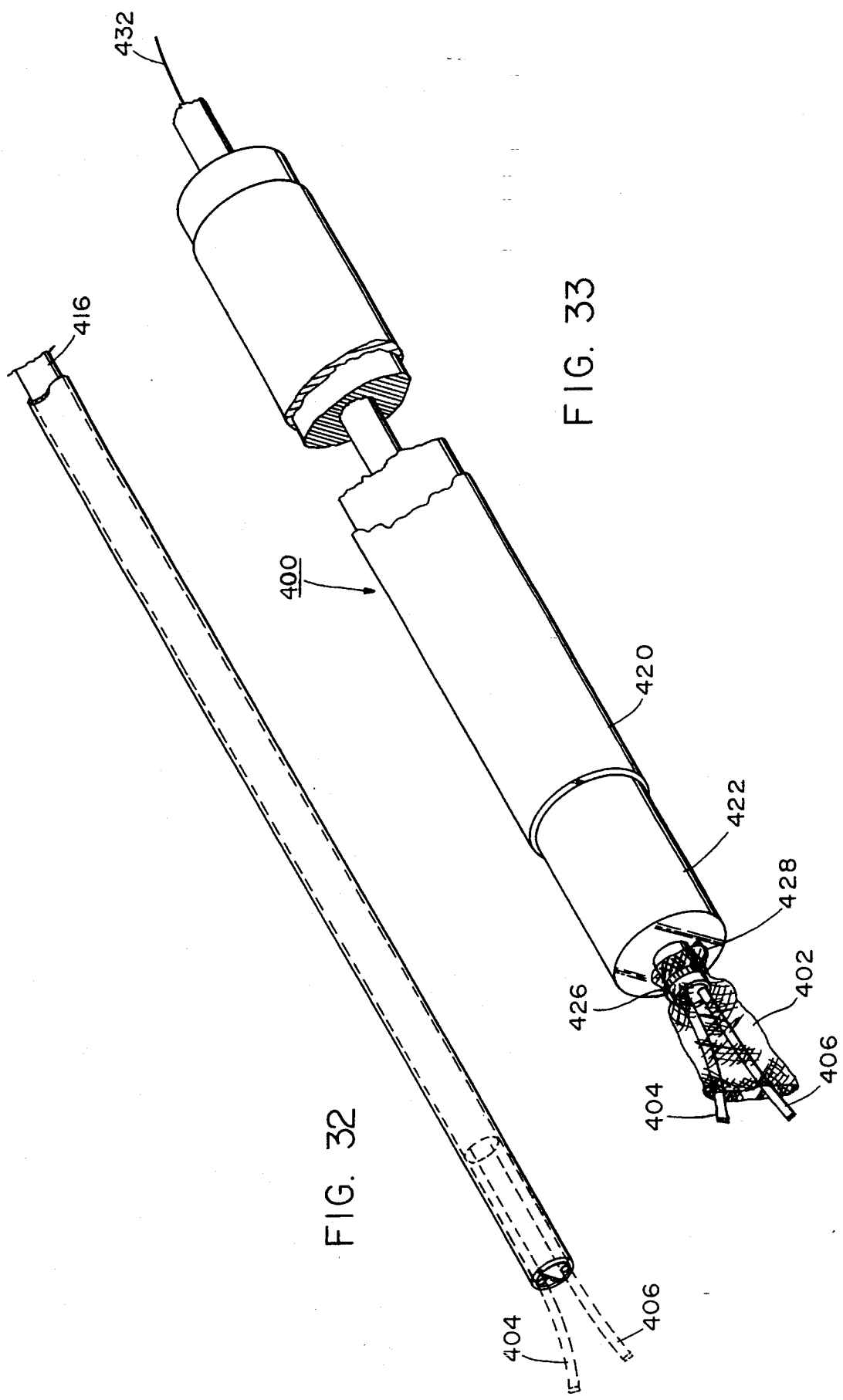

APPARATUS AND METHOD FOR LAPAROSCOPE HERNIA REPAIR

RELATED APPLICATION

This application is a continuation-in-part application of copending U.S. patent application Ser. No. 07/595,956 filed Oct. 11, 1990, now U.S. Pat. No. 5,141,515.

BACKGROUND OF THE INVENTION

SUMMARY OF THE INVENTION

This invention relates to medical apparatus and methods, and, more particularly, to the repair of hernias with a laparoscopic approach and associated delivery and expansion systems.

SUMMARY OF THE BACKGROUND ART

A hernia is one of the most common ailments of mankind. Approximately five percent of the adult male population is affected. Basically, a hernia is a weakness or hole in the abdominal wall through which abdominal contents such as bowels may protrude. Inguinal or groin hernias normally occur at one or more of three locations. The first location is in the weakened wall or inguinal floor of the abdomen in Hesselbach's triangle. This type of hernia is called a direct hernia. An indirect hernia occurs at the internal ring adjacent to the vas deferens as it exits the abdomen to become part of the spermatic cord. The third is a femoral hernia that occurs adjacent and medial to the femoral blood vessels.

All hernias represent a potentially life-threatening condition and once diagnosed they should be repaired unless there is some contraindication.

The surgical repair of an inguinal hernia (inguinal herniorrhaphy) is a common procedure which surgeons often perform on an outpatient basis. It is estimated that 500,000 are performed each year in the United States. According to the procedure, an anesthetic is first administered to the patient and the surgeon then makes a large incision, about 6 inches, in the patient just above the inguinal ligament. Supporting abdominal muscles and fascia are dissected to reveal the hernia sac. The herniated contents protruding through the opening in the abdominal wall are returned to the abdomen. Thereafter, the surgeon closes the hernia sac. The local tissues are then sutured together from opposite sides of the weakened tissue, hole or hernia. The stretched or otherwise weakened tissue may be cut away. Where appropriate, a patch of artificial material may be sutured to the normal tissue to replace the stretched or otherwise weakened tissue or to reenforce over the outside of the repair. The skin incision is then closed over the repair. Recovery time necessary prior to heavy lifting or strenuous labor is usually six to eight weeks and recurrence rates may approach twenty percent.

Another more difficult approach which is less common, but more physiological, is to make an incision in the abdomen superior or cephalad to the hernia. The surgeon cuts through the abdominal wall to the last layer (the peritoneum). Dissection continues in this preperitoneal approach and exposes the hernia defect from the inside. Again direct suture repair or patch repair may be performed. The recurrence rates are low with an inside patch repair because increased intra-abdominal pressure only serves to force the patch more firmly into place to plug the hole similar to a drain plug in a bathtub.

Although common, the standard operational procedures for repair of a hernia is undesirably lengthy and, consequently, costly, requires a large incision with the excessive dissection of normal tissue, causes excessive pain and discomfort to the patient, involves unacceptably long recovery and work disability time, and results in an unacceptably high recurrence rate.

Accordingly, it is an object of the present invention to provide laparoscopic delivery and expansion systems including patches, plugs and patch/plug assemblies.

It is a further object of the present invention to employ laparoscopic techniques for the repair of hernias thereby reducing the length of the incision along with the unnecessary dissection of normal tissue.

It is a further object of the present invention to utilize a new laparoscopic approach via the preperitoneal space.

It is a further object of the present invention to minimize the time and cost of hernia operations.

It is a further object of the present invention to minimize a patient's pain and discomfort associated with a hernia operation.

It is a further object of the present invention to shorten the recovery time normally attendant with a hernia operation.

It is a further object of the present invention to reduce or preclude the recurrence of hernias.

It is a further object of the present invention to provide an improved expansion system for patch expansion.

Lastly, it is an object of the present invention to utilize patches, plugs or patch/plug assemblies for the repair of a hernia wherein the patch has its own memory for assuming its proper orientation over the area to be repaired.

Further objects of the present invention are to internally plug and or patch and restore stretched or weakened areas of an abdominal wall or overt hernia defects and to simultaneously patch all primary and secondary abdominal areas which are predisposed to hernias.

Related prior patents of mine are U.S. Pat. Nos. 5,116,357 and 5,122,155.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with specific embodiments shogun on the attached drawings. For the purpose of summarizing this invention, the invention may be incorporated into an improved apparatus for laparoscopically patching hernias comprising a tubular sheath having a distal end and a proximal end; a tubular plunger located within and moveable with respect to the sheath, the plunger having a proximal end and a distal end with the proximal end of the plunger extending proximally outwardly of the sheath for manipulation by a surgeon; elongated means having a proximal end and a biforcated distal end adapted to form a loop, the proximal end of the elongated means extending proximally outwardly of the sheath for manipulation by a surgeon; and a patch supported on the loop for movement therewith, the patch having passageway means for receipt of the loop to retain the patch in a planar configuration.

The invention may also be incorporated into improved apparatus for use by a surgeon to repair a weakened, deranged portion of the anatomy of a patient comprising a sheath having a distal end positionable within a patient and a proximal end positioned exterior of the patient for manipulation by a surgeon, the sheath being of a length to extend from exterior of a patient through a laparoscopic opening into a surgical cavity of the patient; a prosthesis formed of flexible, essentially inextensible material movable from interior of the sheath to a generally planar orientation at a location adjacent to the deranged portion to be repaired; resilient means associated with the periphery of the prosthesis to effect its opening into a generally planar configuration upon removal from the sheath; and an introducer positioned within the sheath and having a distal end coupled to the prosthesis, the introducer adapted to effect the movement of the prosthesis from interior of the sheath to exterior thereof.

The invention may also be incorporated into an improved apparatus for the plugging of hernias through laparoscopic techniques comprising a tubular sheath having a distal end and a proximal end; a tubular plunger located within and moveable with respect to the sheath, the plunger having a distal end spaced proximally of the distal end of the sheath and a proximal end extending proximally of the proximal end of the sheath; and a plug having a generally cylindrical configuration along its length, the plug being located within the sheath at the distal end and moveable from interior thereof to exterior thereof upon manipulation of the proximal ends of the plunger and sheath by a surgeon.

The invention may also be incorporated into an improved method for the laparoscopic repair of abdominal hernias by a surgeon through the patching of weakened portions of the abdominal part to be repaired comprising the steps of providing a patch formed of flexible, inextensible material and positionable in a plane adjacent to the weakened portions of the abdominal part to be repaired, the patch having elongated passageway means located in the plane of the patch adjacent to the majority of the periphery of the patch; providing an elongated interior ribbon having a biforcated distal end positioned within the passageway means and slidable within the passageway means, the ribbon being sufficiently rigid whereby it may be remotely pushed into the passageway; providing an elongated intermediate cylindrical plunger hav ing an interior slidably receiving the ribbon, the plunger having a distal end coupled to the patch and a proximal end to be manipulated by the surgeon; providing an elongated exterior cylindrical sheath having an interior slidably receiving the plunger, the ribbon and the patch, the sheath having a distal end adjacent to the patch and a proximal end to be manipulated by the surgeon, the sheath being of a length to extend from exterior of a patient through a laparoscopic port into a surgical cavity which includes the part to be repaired; positioning the patch and the distal ends of the ribbon, plunger and sheath into a patient adjacent to the area to be repaired; advancing the patch and plunger from the sheath; advancing the ribbon within the passageway of the patch to expand the patch; coupling the patch to the area to be repaired; withdrawing the ribbon from the patch; separating the patch from the plunger; and withdrawing the ribbon, plunger and sheath from the patient.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 shows a portion of the abdominal wall from the inside where hernias normally occur and also illustrating therein a patch for their repair and the precluding of further hernias.

FIG. 2 is a perspective view of the patch constructed in accordance with the principles of the present invention and as shown in FIG. 1, shogun in association with the patch is an introducer functioning as a delivery assembly for the patch.

FIG. 3 is a sectional view of a portion of the patch shown in FIG. 2.

FIG. 4 is a perspective view of a patch similar to that of FIG. 2, but in mirror image for use on the other side of the patient and illustrating a smaller design as for a child.

FIG. 5 is a perspective illustration of a portion of the introducer including an exterior sheath and plunger/expander assembly.

FIG. 6 is a perspective illustration of the patch of FIG. 4 with the patch introducer of FIG. 5 and with parts broken away to show certain internal constructions thereof.

FIG. 7 is an elevational view, partly in section, of the introducer of FIGS. 2 through 6 but with the patch prior to discharge.

FIGS. 8 through 10 are sectional views of the introducer of FIG. 7 taken along lines 8-8, 9-9 and 10-10 of FIG. 7.

FIGS. 11 through 13 are elevational views, partly in section, of an alternate embodiment of an introducer for the patch.

FIG. 14 is a perspective illustration of a patch delivery assembly constructed in accordance with a further alternate embodiment of the invention.

FIGS. 15 and 16 illustrate a plug useable independently of, or in association with, the apparatus shown in FIGS. 1 through 14.

FIGS. 17 through 19 are elevational views, partly in section, of an introducer for the plug constructed in accordance with yet a further embodiment of the invention.

FIGS. 32 through 35 show an alternate delivery system for a patch.

Similar reference characters refer to similar parts throughout the several views of the drawings.

DETAILED DESCRIPTION OF THE PREFERRED EMBODIMENT

Overview

Figure 20:
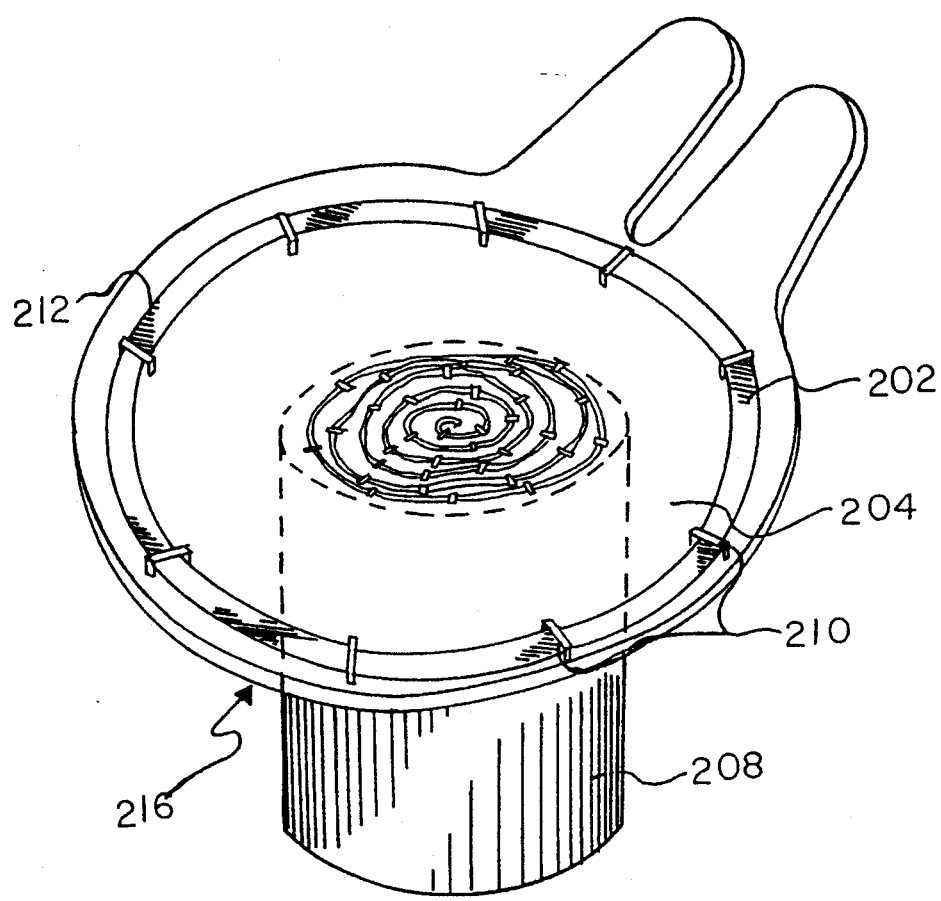
FIG. 20 is a perspective illustration of an alternate plug/flange assembly.

Shown in FIG. 1 is that portion of the abdomen where hernias normally occur. Whether through old age, accident, personal abuse, congenital problems, or the like, the inguinal floor of the abdomen known as Hesselbach's triangle may become weakened to the point whereby inner abdominal contents such as a bowel may protrude. When the organ extending therethrough is a portion of the bowel, serious illness or even death may occur. This is a direct inguinal hernia. There are two other common types of groin hernias. These occur adjacent to either the vas deferens (indirect) or the femoral vessels (femoral hernia). When either the internal inguinal ring through which the vas deferens passes or the abdominal wall adjacent to the femoral vessels becomes enlarged, an opening is created through which abdominal contents such as intestines may protrude thereby constituting a hernia. In the past, surgeons operated upon the hernia area either from above (preperitoneal) or below (anterior) with large incisions which lead to great disability.

The present invention includes introducers 10 with plugs 12 and patches 14, with the patches designed to cover part of or all three areas where groin hernias normally occur and accomplishes a more physiological repair with a smaller incision utilizing laparoscopic technique by use of a specifically designed introducer and patch and a preperitoneal approach presently not used.

Patch and Introducer

The patch 14 is preferably fabricated of a monofilament thread which is woven, knitted or otherwise formed into a fabric which is then cut to a shape. It has a main central portion 16 to cover the inguinal floor area where direct groin hernias normally occur. The shape is generally in the shape of a trapezoid with a major axis and a minor axis.

Extending outwardly from one edge are three asymmetrical portions, formed as three fingers 18, 20 and 22 with the central finger being smaller than the other two. Formed between the fingers are spaced concave recesses, sized and positioned to be placed in close proximity to the vas deferens and or the femoral vessels. Those portions of the patch located adjacent to the recesses are thus adapted to cover those areas of the abdomen where indirect and femoral hernias normally occur. At the same time, the central portion of the patch is adapted to cover the area of the inguinal floor where direct hernias normally occur. The recesses under some circumstances may be not utilized and may be omitted or subsequently cut off.

The threads from which the patch is fabricated are of a surgically clean material which is durable, flexible, essentially inextensible and resistant to corrosion from bodily fluids. By way of example, one acceptable material is polypropylene such as Marlex ® mesh. Marlex is a trademark of the C. R. Bard, Inc. of Murray Hill, N.J. Further, by way of example, one acceptable material thread is Nylon ® polymer. Nylon is a registered trademark of the E. I. DuPont deNemours Company of Wilmington, Del.

Formed into the patch is a passageway 30 for receiving a loop 32, the loop constituting the distal part of the patch delivery assembly or introducer 10. The passageway is shown in the preferred embodiment as spaced axial slits 34 through which the loop is threaded. The passageway may take other forms such as an elongated extent of fabric, preferably of the same material as the patch, secured in a symmetrical manner interior of the periphery of the patch.

When distended, the loop 32 is in the form of an ellipse which has a major axis and a minor axis coextensive with the major axis and minor axis of the patch. In the alternative, the loop and its passageway may take one of many other forms such as that of a teardrop, circle or oval as shown in FIGS. 1, 2, 4, 5, 6, 12, 13 and 14. Other smoothly shaped, curved configurations could be utilized. The periphery of the patch is at varying distances from the passageway and loop. Hence the peripheral portions of the patch do not immediately reach all the areas of direct as well as indirect hernias. Consequently, conventional laparoscopic techniques must be employed by the surgeon to provide final positioning of the patch after initial placement by the loop.

Located within the passageway is the loop 32 of the ribbon 36, constructed of surgically antiseptic material and shaped in a smoothly curved configuration such as an ellipse when expanded. The loop 32 is of a size and configuration to be received within the passageway of the patch 14. The loop is at the far or distal end of the plunger 42. As shown in FIG. 2, the loop of the ribbon holds the majority of the patch in an extended orientation for initial placement on the abdominal wall over the hernia to be repaired. The proximal end of the loop is a ribbon extension of the loop which, like the loop, is flexible, but sufficiently rigid to function in association with the plunger 42 so that a surgeon may remotely push, pull, or rotate the loop and, consequently, the patch, during an operation. The plunger 42 includes a cylinder 44 and guide beam 46. The introducer 10 includes the plunger 42 and sheath 48.

The patch 14 as well as its supporting ribbon loop 32 and its distal extensions 52 are preferably prepackaged in a delivery assembly, the introducer 10, prior to use by insertion through a sleeve which is conventionally placed in a patient by a trochar.

The delivery assembly 10 is best seen in FIG. 7. Its major components include an external cylindrical sheath 48 and an internal plunger 42. The proximal end of the plunger includes a set screw 52 oriented to releasable secure one end of the ribbon. The proximal end of the plunger/expander assembly 42 includes a worm gear 54 for coupling with teeth formed on the ribbon. Note FIG. 8. The worm gear 54 is a preferred mechanism since it permits precise adjustments in the moving of the loop and patch. In this manner, the surgeon may effect the precise movement of the loop in either direction but prevents the inadvertent movement thereof. A cylindrical guide beam 46 with flat faces is located interiorly along the length of the introducer 10 to act as a bearing surface during operation of the set screw 52 and worm gear 54 and for guiding the movement of the ribbon 36 with respect to the plunger 42 during the blooming of the patch. A weld 56, a dot of glue, or the like couples the proximal end of the patch to the distal end of the plunger.

In operation and use, the introducer 10 is inserted through the sleeve with its distal end adjacent to the area of the abdominal wall to be patched. The plunger/expander 42 and patch 14 are pre-positioned within the sheath 48 as shown in FIG. 7. The introducer 10 then is moved forward by the surgeon moving the introducer with respect to the sleeve or withdrawing the sleeve with respect to the introducer. The ribbon, loop and patch move with the introducer when relative movement occurs between the sleeve and introducer. The plunger is depressed to dispense the main body of the patch. Thereafter, the surgeon rotates the knob 58 of the worm gear to enlarge the loop and cause the patch to bloom into the anatomically desired orientation as shown in FIGS. 1, 2 and 13. Using a second laparoscopic opening, the surgeon will position the edges of the patch into final position. The patch will remain in position due to the pressure applied to it by the normal abdominal contents. Staples or sutures could be employed to further secure the patch in its final position.

Alternate Embodiment

The FIG. 11 through 13 embodiment illustrates an alternate introducer for holding the patch and for pushing it outwardly from the distal end of the sleeve. In this embodiment, the ribbon 62 is formed with an enlargement or block 64 at its distal end. The block has a slot 66 through which the ribbon passes to form a loop 68, in a manner similar to a lasso, which supports a patch 70 as in the prior embodiment. The slot is preferably formed with a ratchet tooth to sequentially engage ratchet teeth on the ribbon to allow for only one way movement of the ribbon during blooming of the patch.

The proximal end of the block is not coupled to the distal end of the plunger. Further, the proximal end of the patch is coupled to the distal end of the block as by a weld 74 to hold the proximal end of the patch in position as the distal end of the ribbon is moved distally to effect the blooming of the patch. The guide beam 76 has one flat side to receive and guide the ribbon 62 for movement with respect to the plunger cylinder 78 during the blooming of the patch 70.

In this embodiment, the distal end of the sheath 88 has axially slits 82 at a plurality of locations with the end forming a slight taper or bend. In this manner, the plunger 86 may be moved with respect to the sheath 88, from the FIG. 11 position to the FIG. 12 position. The surgeon can feel the slight resistance caused by the block 64 against the bend indicating that the FIG. 12 position has been reached. Thereafter, the proximal end of the ribbon may be fed distally with respect to the plunger and block to effect the blooming of the patch. Thereafter, the block is moved distally a greater distance until the FIG. 13 position is reached and the resistance to movement is no longer felt by the surgeon, thus freeing the patch from the introducer. The patch 70, loop 68 and block 64 are then cut free of the plunger 86 and the remainder of the ribbon.

Further Alternate Embodiment

In yet a further embodiment of the introducer 90, that shown in FIG. 14, the ribbon 92 is replaced by a looped monofilament thread. The monofilament thread is preferably of a surgically antiseptic, durable, inextensible material. By way of example, acceptable materials are Nylon, polypropylene and polyglycolic acid including PDS. PDS is a tradename of the Johnson and Johnson Company of Sommerville, N.J. These typical materials will allow the threads to be pushed from the introducer by the surgeon. The thread is shaped with a loop 94 received at its distal end. The proximal ends of the thread are for pushing and pulling the thread, and consequently blooming the patch, with respect to the plunger and sheath.

An intermediate portion of the thread is formed with an eyelet 96 adjacent to the proximal end of the plunger for the sliding passage of the proximal end of the thread. As in the embodiment discussed immediately hereinabove, the loop supporting the patch is formed as a lasso. The two proximal ends of the thread are manipulated by a surgeon during operation and use. A guide beam 98 shaped as an I-beam is incorporated within the plunger to guide the movement of the thread ends with respect to the plunger during the blooming of the patch. There is no need for a direct attachment of the loop to the plunger as this occurs passively. There is, however, a need for coupling the patch to the eyelet for proper patch placement. With the thread and patch dispensed outside the sheath as described above, the proximal end of the thread end passing through the eyelet is pushed so that a central extent of the thread begins to move forward out of the sheath to effect the blooming of the patch.

In all of the embodiments requiring thread removal, after final positioning of the patch, the proximal end of the patch must be cut from its attachment from the introducer, block or eyelet ribbon while the distal end of the loop must be cut so that the introducer and ribbon may be withdrawn from the patch and site of the operation.

In the embodiments of FIGS. 4 and 11 through 13, when the loop is formed of an absorbable material, the loop must be cut free of the remainder of the ribbon.

It should be understood that a wide variety of mechanisms could be used to support the patch and to effect its blooming and positioning. In the disclosed embodiments herein, the monofilament thread could be replaced by a ribbon and the ribbon could be replaced by a monofilament thread. Further, a wide variety of materials could be substituted between the thread embodiment and ribbon embodiments including the use of absorbable, biodegradable or biocompatible materials for the loop that need not be removed. One typical material is a copolymer of glycolide and lactide of the type marketed under the tradename Vicril by Ethicon, a division of Johnson & Johnson of Somerville, N.J.

Note is taken that the FIG. 14 embodiment illustrates the introducer 90 with a slight curve. This slight curve allows the surgeon to more readily axially rotate the introducer and thus the patch, for a more precise patch positioning. Such curve may also be utilized in the plug introducer assembly discussed hereinafter. The introducer may be of a slightly flexible nature. Conventional straight or flexible sleeves may, of course, also be employed.

One distinguishing characteristic of the present invention is the shaping of the distal end of the introducer with a bevel 102. This will allow the surgeon to view the orientation of the introducer and patch on a monitor or through an operating laparoscope prior to moving the patch from the interior of the introducer. In addition, radiopaque markers 104 on the patch and/or plug could be utilized for determining their orientation and location by conventional radiographic techniques.

Plug and Introducer

Plugs are shown in FIGS. 15 and 16 while their introducer 110 is shown in FIGS. 17 through 19. The FIG. 15 plug 12 is simply a piece of surgical fabric or mesh such as Marlex® mesh. The material is spirally wrapped to form a mending component in a generally cylindrical shape. The term generally cylindrical shape is intended to include components which have a taper, as for example a truncated cone. It may also be fabricated as a one piece molded object of an open cell foam of a sponge like nature.

The FIG. 16 plug 112 is similar in construction to the FIG. 15 plug 12. It includes, in addition, a flange 114. The flange is preferably fabricated of a material similar to the patch. The flange may be with or without one peripheral edge that includes a radial extension with two symmetric fingers 118 and 120 and a recess 122 for receiving an adjacent vas deferens or femoral blood vessels. The central plug component may be of an absorbable or biodegradable material to be assimilated into bodily tissue over time. The plug is also preferably formed with openings or interstices to accelerate the healing of the opening being patched through the promoting of scar tissue in growth. The plug may be made of a material such that it expands and swells if exposed to fluids. A sponge is typical of such a material.

The plug introducer assembly 110 is seen in FIGS. 17, 18 and 19. During operation and use, the assembly is positioned through a sleeve. The assembly includes an exterior cylindrical sheath 128 and an interior cylindrical plunger 126. As seen in FIG. 17, the plug is initially located in the distal end of the sheath with the flange, if utilized, at the proximal end of the plug. The plunger is proximally located with respect to the plug.

As is conventional in the arts, laparoscopic trocars have an inner diameter of from about 0.5 to 1.5 centimeters. Consequently, the plug diameter when packaged in the sheath, as shown in the various Figures, is slightly less than between 1.0 and 1.2 centimeters. The plug length is sufficient to be retained within the typical hernia defect which is generally of a length at least equal to the diameter of the plug, at least about 1.0 to 3.0 centimeters, the thickness of the abdominal musculature. Plugs may be greater in length depending on the requirement of the anatomy but should be as short as possible to avoid external palpation. In addition, the flange is about one to three times the diameter of the plug, about 0.5 to 4.5 centimeters, measured radially from the radially exterior of the plug. The flanges may be greater in size, twice as large as shown or even larger, depending upon the nature of the anatomy and the body portions available to which the flange will be secured to the patient. The flange may be eliptical, square, rectangular, trapezoidal in configuration.

In operation and use, the distal end of the introducer and plug is simply inserted into the hernia defect 132 and dispensed by depressing the plunger while withdrawing the sheath thereby leaving the plug in place. Additional plugs may be placed to fill the defect if excessively large. Alternatively the plug with flange may be inserted to plug the defect and support the adjacent weak tissue. The dispensing of the plug may be effected by any relative movement between the plunger and sheath, by moving the plunger with respect to the sheath or the sheath with respect to the plunger. FIG. 18 illustrates the plug in the tissue opening after being dispensed. FIG. 19 illustrates the plug without a flange. Handles at the proximal ends of the sheath and plunger assist the surgeon in this procedure. Once placed within the tissue to be repaired, the plug or plugs may be caused to swell to a larger diameter through being irrigated either naturally through bodily fluids or artificially as through a saline solution introduced by the surgeon.

Method

The plug, plug/flange assembly, and patch and their delivery apparatus may be utilized independently of each other or sequentially in system configuration, depending on the condition of the patient and the parts of the body to be repaired. The utilized mending component, whether plug or plug with flange or patch, are at the discretion of the surgeon.

During an operation, the operating laparoscope, sleeve with its contents, is positioned within the incision into the preperitoneal space. The space is dissected with insufflation of carbon dioxide or other conventional gas technique. The laparoscope and its contents are manipulated inwardly and outwardly thereof for effecting the appropriate procedures. After dissection of the space, other punctures in the abdomen are made for placement of a second or third sleeve. These additional sleeves allow for use of additional instruments for manipulation, dissection, and use of a laser or cautery. Similarly, the patch and/or plug introducers and contents are manipulated inwardly and outwardly of the sleeves.

To position the plug in its orientation adjacent to the intended area, the plug is positioned within the distal end of the introducer. The plug is initially packaged within the introducer. The introducer and its contents are advanced to within the hernial defect which is to receive the plug. The surgeon holds the proximal end of the plunger forward while the sheath is withdrawn. The plug will then move outside of the sheath into the position of FIG. 18. The plunger holds the plug against movement while allowing complete release from the sheath. Additional plugs may be inserted as needed.

To position the patch in its orientation adjacent to the intended area, the patch is positioned on the loop and located within the distal end of the introducer. The introducer and its contents are advanced to a position adjacent to the area of the abdominal wall which is to receive the patch. The patch is dispensed by the surgeon pushing the proximal end of the plunger distally while moving the sheath proximally. The patch will then move outside of the introducer with the loop resiling to the elliptical shape of FIGS. 1 and 2. The blooming of the patch is effected by the extending of the loop within the patch thus distending the patch to a proper, anatomically correct shape. Such patch is a passive patch since an external force is needed to effect its expansion. This procedure may be observed by the surgeon through conventional laparoscopic techniques.

With the central portion of the patch properly positioned, the surgeon may manipulate the edges of the patch exterior of the loop, and secure the patch in proper position. Staples or sutures could be utilized but the contents of the abdominal cavity may be sufficient to apply adequate pressure to hold the patches in proper position. With the patch having been secured around its periphery as shown in FIG. 1, the ribbon may be removed from the patch prior to the withdrawal of the introducer. Once again, conventional laparoscopic techniques may be employed to cut the ribbon at its distal end so that the ribbon may be slid from the passageway and withdrawn prior to removal of the introducer. This step is eliminated if the loop is of a degradable material. The patch and loop must then be cut away from the plunger prior to removal of the introducer.

The present invention may be utilized by a surgeon in carrying out a new laparoscopic procedure for repairing hernias.

Alternate Patches, Plugs and Patch/Plug Assemblies

Shown in FIGS. 20–24 are alternate embodiments of the present invention. In accordance with the alternate embodiments, the plugs are constructed as discussed previously in the prior embodiment of FIG. 16. A flange coupled to each plug is also included as discussed previously to constitute plug/flange assemblies. In the prior embodiment, however, it is up to the surgeon to position the flange over the area of hernial weakness through tweezers in a laparoscopic procedure.

Figure 21:
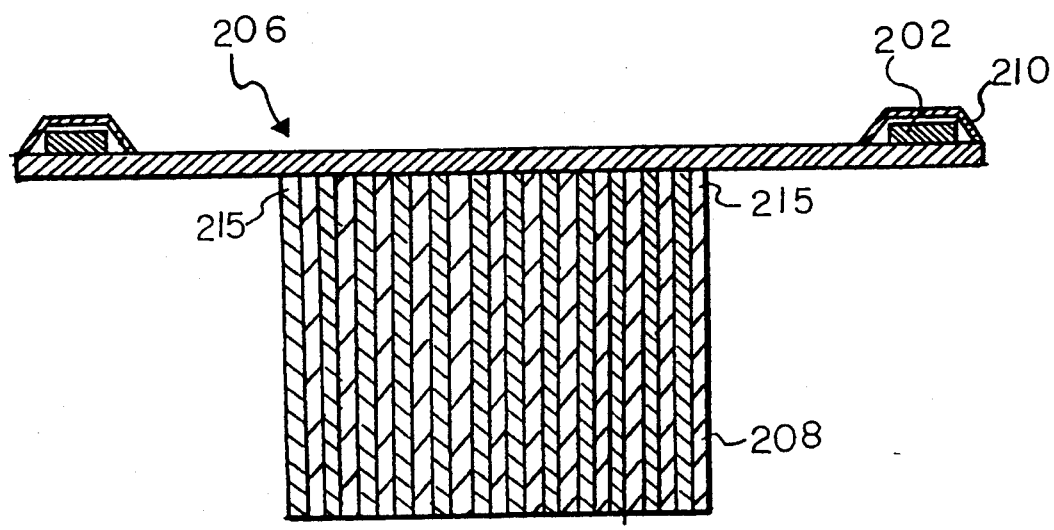
FIG. 21 is a sectional view of the assembly shown in FIG. 20 taken along line 21—21 of FIG. 20.

According to the alternate embodiment of FIGS. 20 and 21, a washer-shaped member 202, generally with a rectangular-cross-sectional configuration, of a resilient, elastomeric material, is coupled to the flange 204 in a circle adjacent to the periphery of the flange. In this manner, the washer-like member functions to return the flange 204 to the orientation as shown in FIG. 20 after being stored in a constricted configuration within a sleeve prior to utilization. The time and effort expended by a surgeon for positioning of the flange 204 is, consequently, eliminated. While stored in the sleeve, the flange 204 and its resilient member 202 are withdrawn to a constricted configuration prior to being ejected from the sleeve and placed in the body part to be repaired. In the FIG. 20 showing, the central portion of the flange is removed to show the internal construction of the plug.

The terminology plug, flange and patch are used for illustration purposes. When patching material is coupled to a plug it is called a flange but its function is to augment or restore structural integrity of the weakened abdominal wall just as the patch alone.

Prior to placement of the patch/plug assembly or device 206, the entire patch/plug assembly with its plug 208 and washer-like member 202 are located within the sleeve for being dispensed as previously discussed. As a result, dispensing of the assembly from the sleeve and locating the plug in the hernial opening will automatically position the flange in a proper orientation. A mark on the sleeve, detectable by laparoscopic observation as discussed hereinabove, is positioned on the sleeve and correlated to a predetermined portion of the flange, preferaby the enlarged portion. This precludes the need for rotational orientation of the flange and ensures the proper level of insertion of the plug. If re-orientation of the plug is needed to reposition the flange, such re-orientation would have to be done laparoscopically as through tweezers, but the flange blossoming is still eliminated.

In this FIG. 20 embodiment, the washer-like element has a rectangular cross sectional configuration with a radial dimension of between about 0.15 and 0.25 centimeters and an axial dimension of between about 0.05 and 0.10 centimeters. The entire washer like element has an exterior diameter of between about 4.0 and 6.0 centimeters for allowing positioning in the sleeve when in a constricted configuration. The exterior diameter is substantially equal to the diameter of the majority of the flange.

Coupling of the washer-like element to the flange may be done through stitching 210 or weaving. In the alternative, it may be woven in and out of threads of the flange. Such weaving embodiment requires that the washer-like element be provided with a radial cut 212 so that the weaving may be effected. After weaving and before use, however, the cut is preferably sealed as by welding. It may also be coupled by adhesive or glue. Stitching 211 around the periphery of the plug couples the plug to the flange. In the alternative, an appropriate adhesive could be utilized. The washer-like element could also be placed between two coextensive patches coupled together.

A further modification of the FIG. 20 embodiment involves the shaping of a resilient element 214 in a serpentine configuration. Stitching of such serpentine resilient element 214 is the same as in the FIG. 20 embodiment and the desired resilience and positioning is accomplished properly. By constructing the washer-like element 214 in the serpentine manner rather than circular as like men%bet 202 allows the more even distribution of volume within the sleeve prior to operation and use. In other words, the volume of the washer-like element is spread more evenly along the length of the plunger and sleeve at the distal ends thereof.

Figure 22:
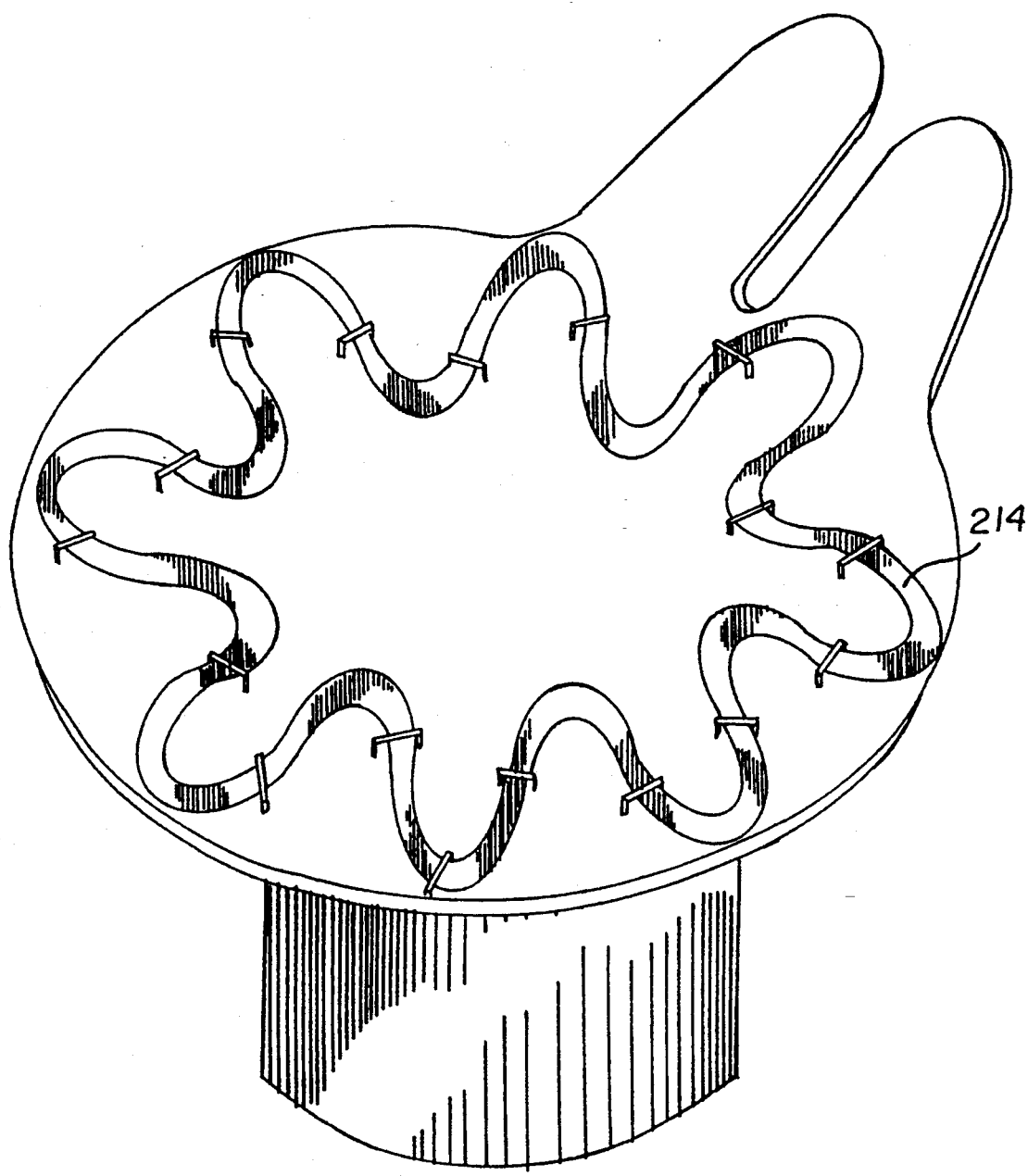
FIG. 22 is a perspective illustration of a modified resilient member for use with the assembly of FIG. 20.
Figure 23:
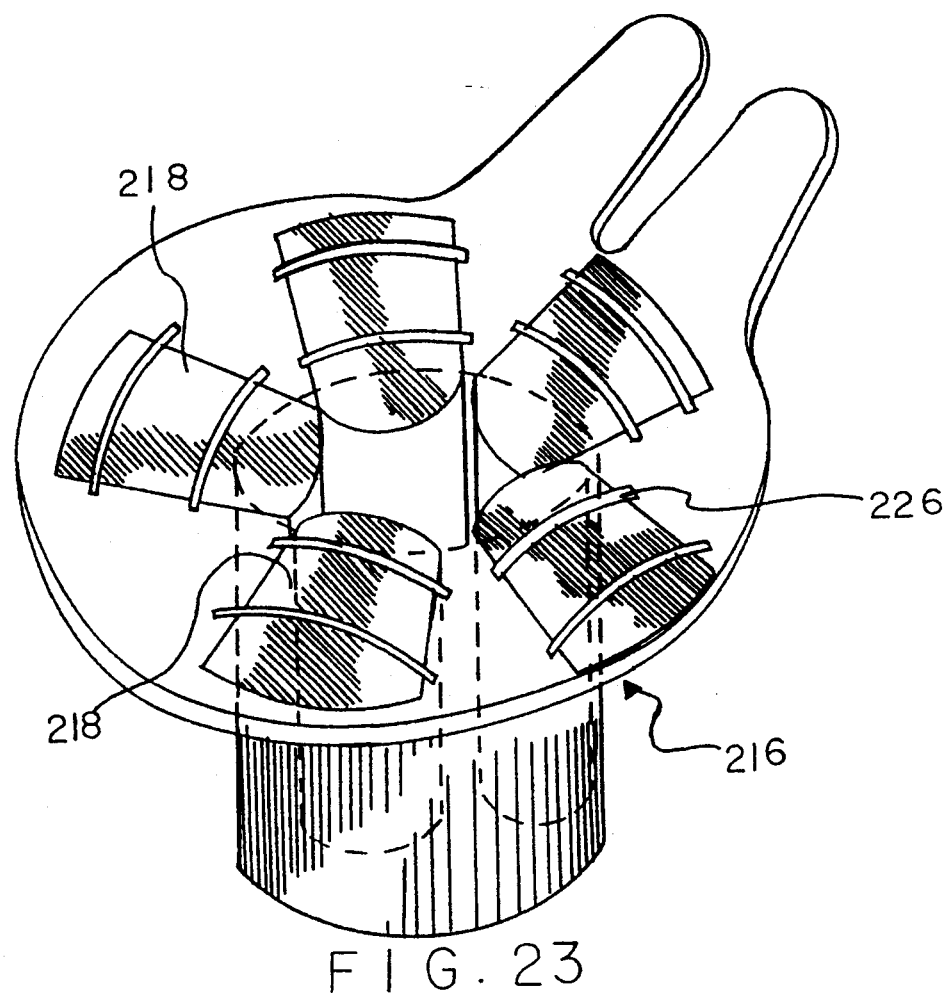
FIG. 23 is a perspective illustration of an additional alternate plug/flange assembly.
Figure 24:
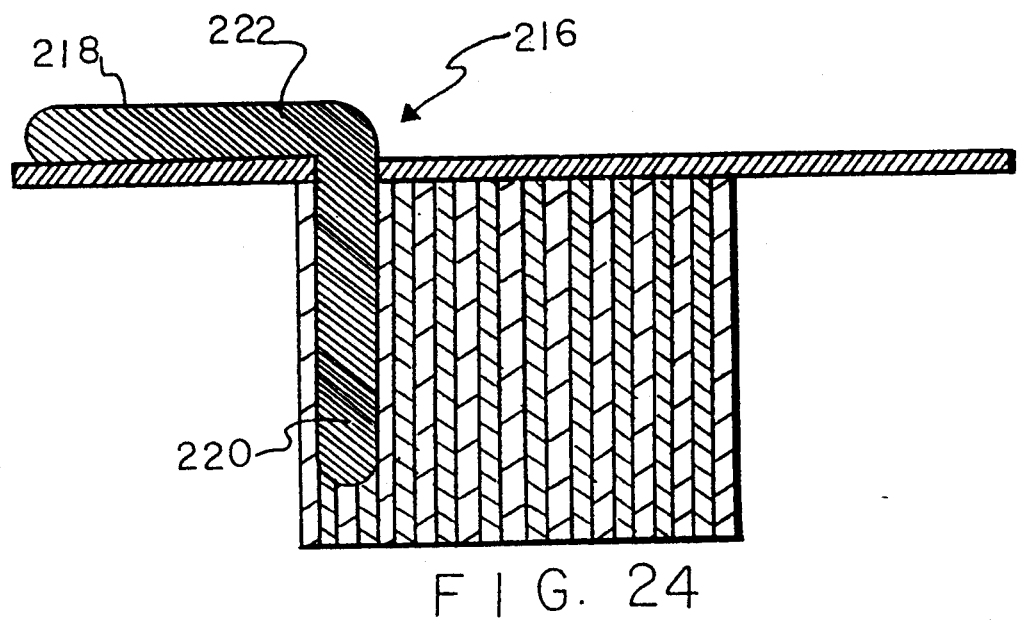
FIG. 24 is a sectional view of the assembly shown in FIG. 23 taken along line 24—24 of FIG. 23.

FIGS. 23 and 24 illustrate yet a further alternate embodiment of the plug/flange assembly 216. In this embodiment, the washer-like element is replaced with a plurality of resilient L-shaped members 218. One leg 220 of each L-shaped member is located within an exterior layer of the plug 208 wrapping material, parallel with the axis of the plug. The other leg 222 of each L-shaped member 218 extends radially outwardly from the plug to a distance just short of the external periphery of the flange 204. Five such L-shaped members are shown in the FIG. 22 illustration of this embodiment, fanning outwardly in a symmetric starburst configuration. A lesser number could be utilized so long as it continues to function in spreading out the flange in its intended generally planar configuration. A greater number could also be utilized so long as it continues to function in spreading out the flange and can be fit within the sleeve during storage and prior to use. The legs 220 and 222 of the L-shaped members 218 are coupled to the flange material through stitching 226 as shogun, or they may be woven through the fabric at spaced apart points. The individual L-shaped members 218 are formed of a resilient material, metal, plastic, or other biocompatible material to assume the natural configuration with a right angle bend therein, as shown. They are also adapted to be bent into a linear or essentially linear orientation when stored within the sleeve with the plug/flange assembly prior to use. Each L-shaped member has legs which are between about 1.5 and 4.0 centimeters in length, between about 0.2 and 0.5 centimeters in width and between about 0.10 and 0.20 centimeters in thickness with the bend located to coincide with the junction of plug and flange, generally at about the midpoint. The sizes are variable as a function of the size of the channel, the thickness of the patch material, the plug size, extent of the hernial weakness, hernial opening, etc.

Prior to placement of the plug/flange device 206, the entire plug/flange device with its plug 208 and L-shaped members 202 are located within the sleeve for being dispensed as previously discussed. As a result, dispensing of the assembly from the sleeve and locating the plug in the hernial opening will automatically position the flange in a proper orientation.

The flange and plug are, as in the prior embodiments, preferably fabricated of a material which is not absorbable by the patient's body through the passage of time. The resilient material may, however, be biodegradable by the patient's body since its function is completed upon the proper positioning of the flange during the surgery.

Figure 25:
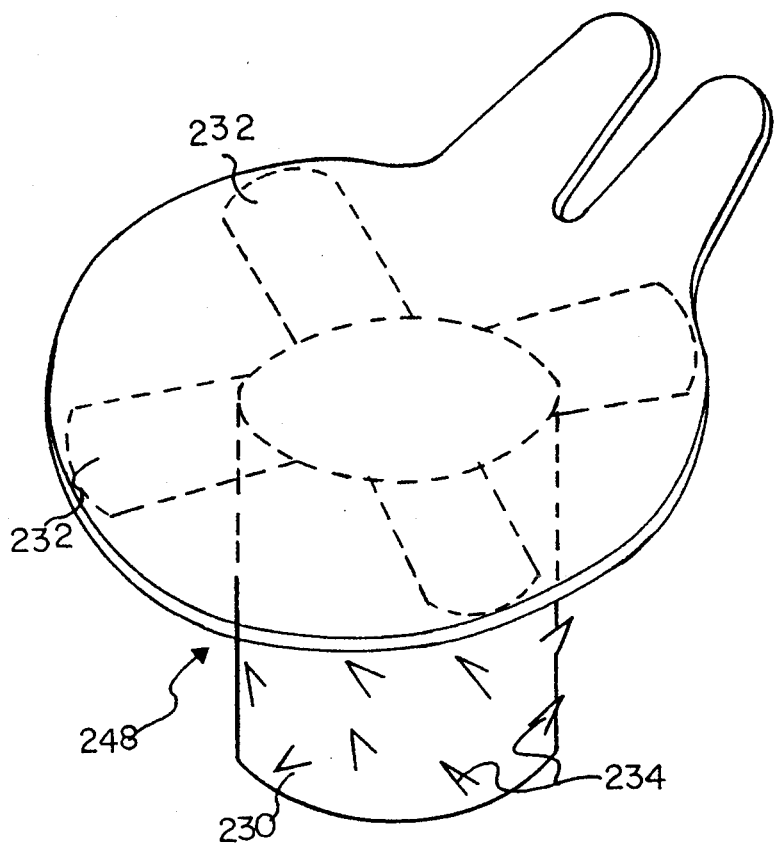
FIG. 25 is a perspective illustration of an additional alternate plug/flange assembly.
Figure 26:
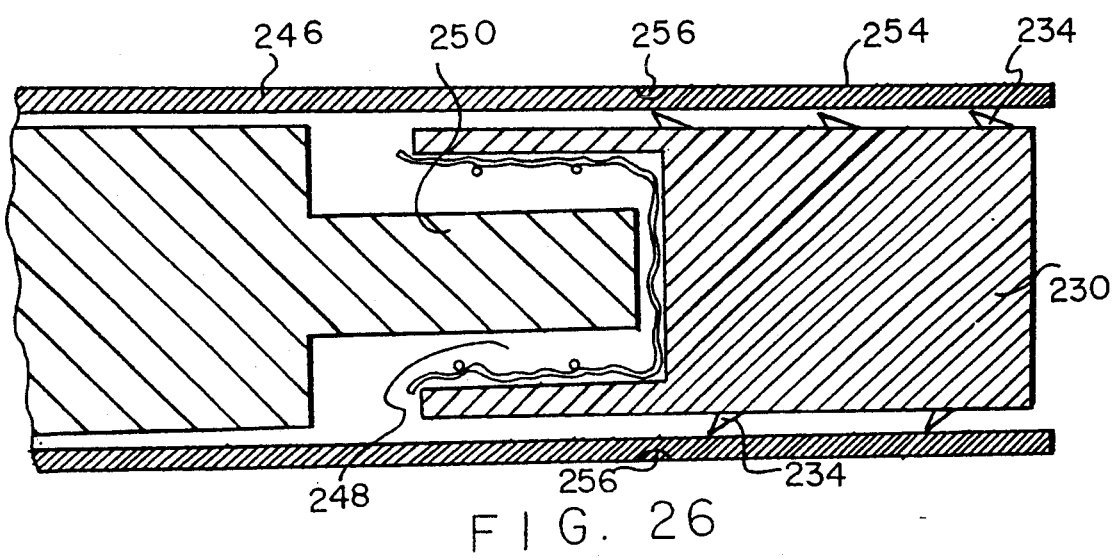
FIG. 26 is a plan view of a modified plunger for accommodating the alternate plug/flange assemblies of FIGS. 20-24 with parts removed to show internal constructions.

The FIG. 25 embodiment illustrates a plug 230 fabricated of a one piece molded construction. Such plug/flange assembly is also seen in cross sectional view in FIG. 26 where it is loaded in a sheath for being dispensed. Extending proximally from the plug are the resilient men%bets 232 formed integrally with the plug for functioning as in the prior embodiments of the plug/flange assemblies. FIG. 26 shows the resilient members prior to being dispensed. FIG. 25 shows the resilient members after moving to their natural orientation. In this embodiment, the exterior surface of the plug 230 is roughened to increase its frictional contact with the tissues and maintain its position within the patient. In the alternative, needle-like projections 234 may be molded into the exterior surface of the plug as shogun in FIGS. 25 and 26. This also increases the frictional contact between the plug and the tissues. The projections preferably extend generally radially from the plug and are angled proximally thereof.

An alternate plunger is shown in FIG. 26. The plunger is located within a sleeve as in the prior embodiments with the plug/flange assembly at the distal end thereof. In order to accomodate the added volume of the flange generated by either washers 202 or 214 or the L-shaped members 218, the distal end of the plunger 244 is of a reduced diameter to generate a space 248 therearound and within the sleeve 246 for accommodating the volume of the flange and its resilient member or members. In this manner, the distal end 250 of the plunger may contact the proximal end of the plug for inserting the plug in the appropriate hernial opening.

As referred to hereinabove, markings are preferably formed on the sleeve to indicate the linear and rotational orientation of the sleeve and, hence, the flange. To that extent an axial marking 254 on the sleeve 246 extends proximally from the distal ed to a location for indicating the proximal end of the plug and the enlarged portion of the flange. A circumferential marking 256 extends around the sleeve 246 to indicate the proximal end of the plug. Either one or both or alternate markings could be utilized for these purposes. Such markings could be visually observable or of a radiopaque material as is well known in the arts.

Figure 27:
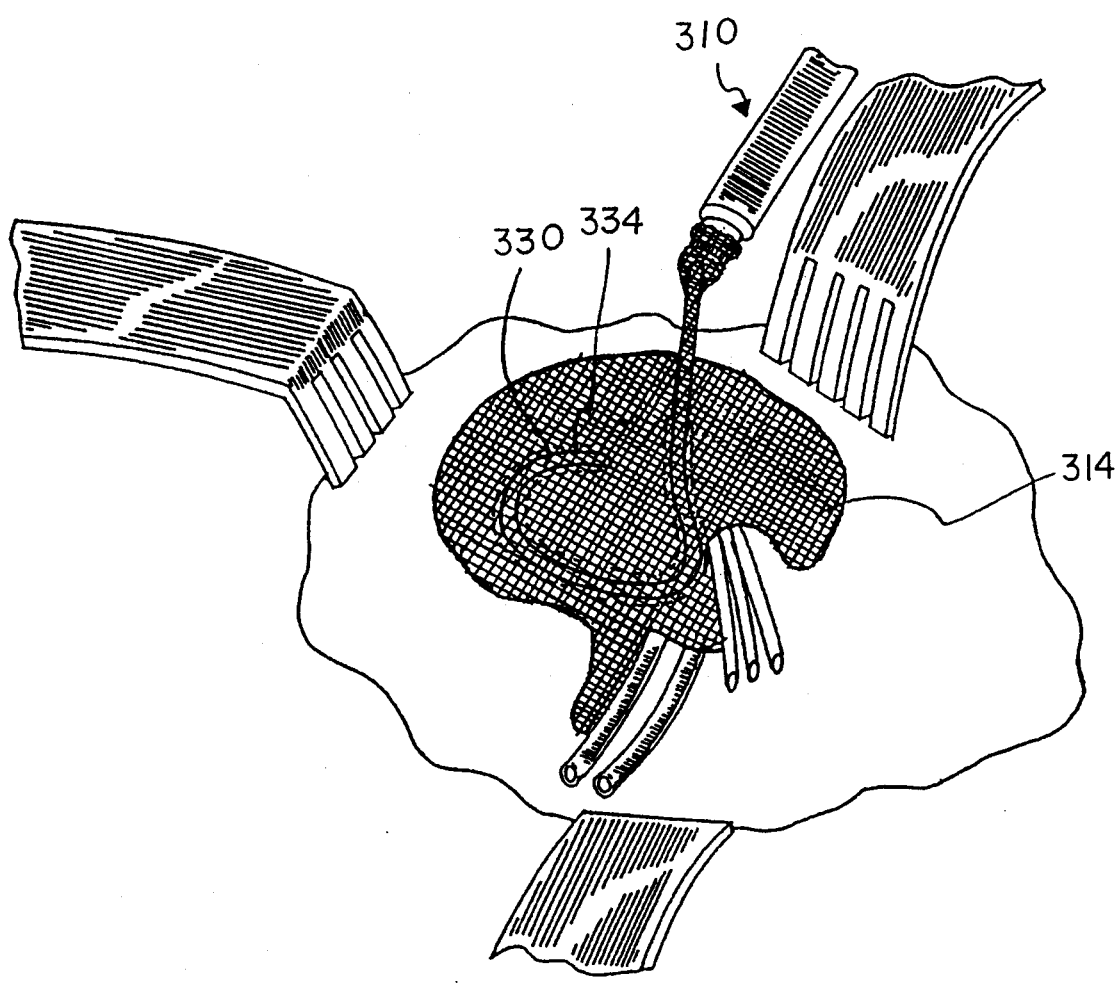
FIG. 27 shows a portion of the abdominal wall from the inside where hernias normally occur and also illustrating therein a patch for their repair and the precluding of further hernias.
Figure 28:
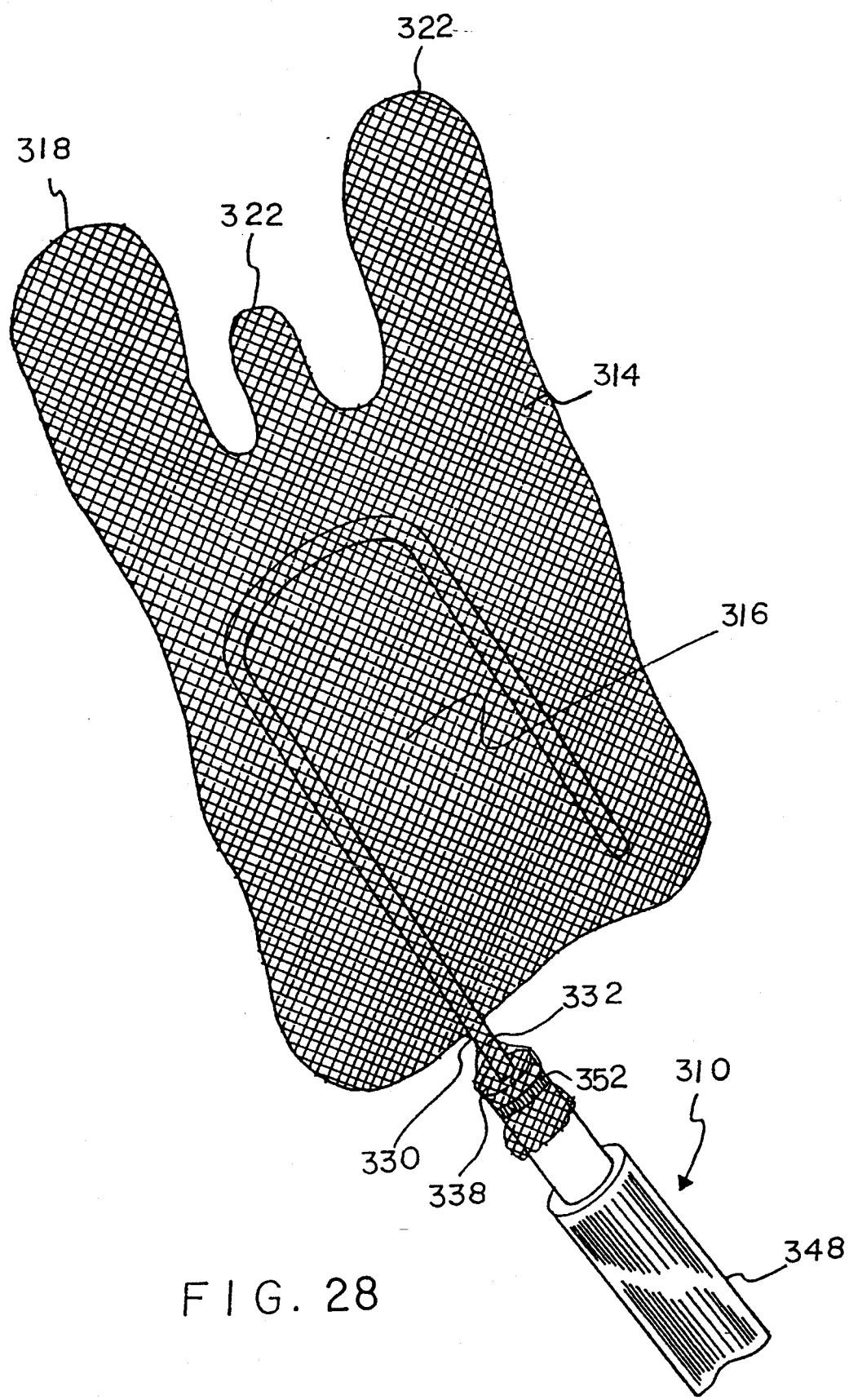
FIG. 28 is a perspective view of a patch constructed in accordance with the principles of the present invention similar to that shown in FIG. 1, illustrated in association with the patch is an introducer functioning as a delivery assembly and system for the patch.

Shown in FIG. 27 is that portion of the abdomen where hernias normally occur. Whether through old age, accident, personal abuse, congenital problems, or the like, the inguinal floor of the abdomen known as Hesselbach's triangle may become weakened to the point whereby inner abdominal contents such as a bowel may protrude. When the organ extending therethrough is a portion of the bowel, serious illness or even death may occur. This is a direct inguinal hernia. There are two other common types of groin hernias. These occur adjacent to either the vas deferens (indirect) or the femoral vessels (femoral hernia). When either the internal inguinal ring through which the vas deferens passes or the abdominal wall adjacent to the femoral vessels becomes enlarged, an opening is created through which abdominal contents such as intestines may protrude thereby constituting a hernia. In the past, surgeons operated upon the hernia area either from above (preperitoneal) or below (anterior) with large incisions which lead to great disability.

The present invention includes an introducer 310 with a prothesis which in the preferred embodiment is a patch 314, with the patch designed to cover all three areas where groin hernias normally occur and accomplishes a more physiological repair with a smaller incision utilizing laparoscopic technique by use of a specifically designed introducer and patch and preperitoneal approach presently not used. The prothesis is also adapted to be used on other deranged areas of a patient where repair is needed.

The patch 314 is a preferably fabricated of a monofilament thread which is woven, knitted otherwise formed into a fabric which is then cut to a shape. It has a main central portion 316 to cover the inguinal floor area where direct groin hernias normally occur. The shape is generally in the shape of a trapezoid with a major axis and a minor axis.

Extending outwardly from one edge are three asymmetrical portions, formed as three fingers 318, 320 and 322 with the central finger being smaller than the other two. Formed between the fingers are spaced concave recesses, sized and positioned to be placed in close proximity to the vas deferens and or the femoral vessels. Those portions of the patch located adjacent to the recesses are thus adapted to cover those areas of the abdomen where indirect and femoral hernias normally occur. At the same time, the central portion of the patch is adapted to cover the area of the inguinal floor where direct hernias normally occur.

The threads from which the patch is fabricated are of a surgically clean material which is durable, flexible, essentially inextensible and resistant to corrosion from bodily fluids. By way of example, one acceptable material is polypropylene such as Marlex mesh. Marlex is a trademark of the C. R. Bard, Inc. of Murray Hill, N.J. Further, by way of example, one acceptable material thread is Nylon polymer. Nylon is a registered trademark of the E. I. DuPont deNemours Company of Wilmington, Del.

Formed into the patch is an ellipse shaped passageway 330 for receiving the far or distal end of an interior ribbon 332. In the passageway, the ribbon forms a generally ellipse shaped loop which constitutes the distal part of the patch delivery assembly or introducer 310. The passageway is shown in the preferred embodiment as a supplemental piece of patch material of a tubular fabric generally attached to the patch in the shape of an ellipse. The supplemental piece is preferably a tube coupled to the patch by stitches 334, or by glue or the like or may be fabricated in continuity in the patch. The coupling is at a location adjacent to the periphery of the patch and the periphery of the supplemental piece except at one end through which the ribbon extends. The ribbon preferably has a flat cross sectional configuration to promote its handling. Specifically, the longer flat face of the ribbon always extends parallel with the axis of the loop which it forms. Stability of the loop shape is enhanced which allows rotation of the ribbon during operation and use while maintaining such loop shape.

When distended, the loop 332 is in the form of an ellipse which has a major axis and a minor axis coextensive with the major axis and minor axis of the patch. In the alternative, the loop and its passageway may take one of the many other forms such as that of a teardrop, circle, oval or the like. Other smoothly shaped, curved configurations could be utilized. The periphery of the patch is at varying distances from the passageway and loop. Hence the peripheral portions of the patch may not necessarily immediately reach all the areas of direct as well as indirect hernias. Consequently, conventional laparoscopic techniques may be necessary by the surgeon to provide final positioning of the patch after initial expansion of the loop.

Located within the passageway is the loop of the ribbon 332, constructed of surgically antiseptic material and shaped in a smoothly curved configuration such as an ellipse when expanded and constrained by the passageway. The ribbon 332 is of a size and configuration to be received within the passageway of the patch 314. The loop exits at the distal end 338 of the intermediate plunger 342. As shown in the Figures, the loop of the ribbon holds the majority of the patch in an extended orientation for initial placement adjacent to the abdominal wall over the hernia to be repaired. The distal end of the ribbon is of a bullet shape, generally hemispherical, so as to facilitate smooth movement within the passageway. In the alternative, the endmost part of the ribbon could be simply bent inwardly toward the center of the patch to effect the same result. The near or proximal end of the loop is a ribbon extension of the loop which, like the loop, is flexible, but sufficiently rigid to function in association with the plunger 342 so that a surgeon may remotely push, pull, or rotate the loop and, consequently, the patch, during an operation. The plunger 342 is a hollow cylinder through the ribbon passes. The introducer 310 includes the plunger 342 and a cylindrical exterior sheath 348.

The proximal end of the patch 314 includes an extension of the tubular component, the passageway 330, attaching to the distal end of the plunger so that the ribbon is at all time enclosed by the passageway. Coupling is preferably through a C-shaped spring clamp 352 installed at fabrication in a circular recess 354 on the plunger. Other coupling techniques include thread, glue, tape, or the like. Further, the attached tubular component could be coupled to the interior or end of the plunger. This coupling of patch and plunger assists the surgeon in the proper positioning of the patch on the area to be repaired.

Figure 29:
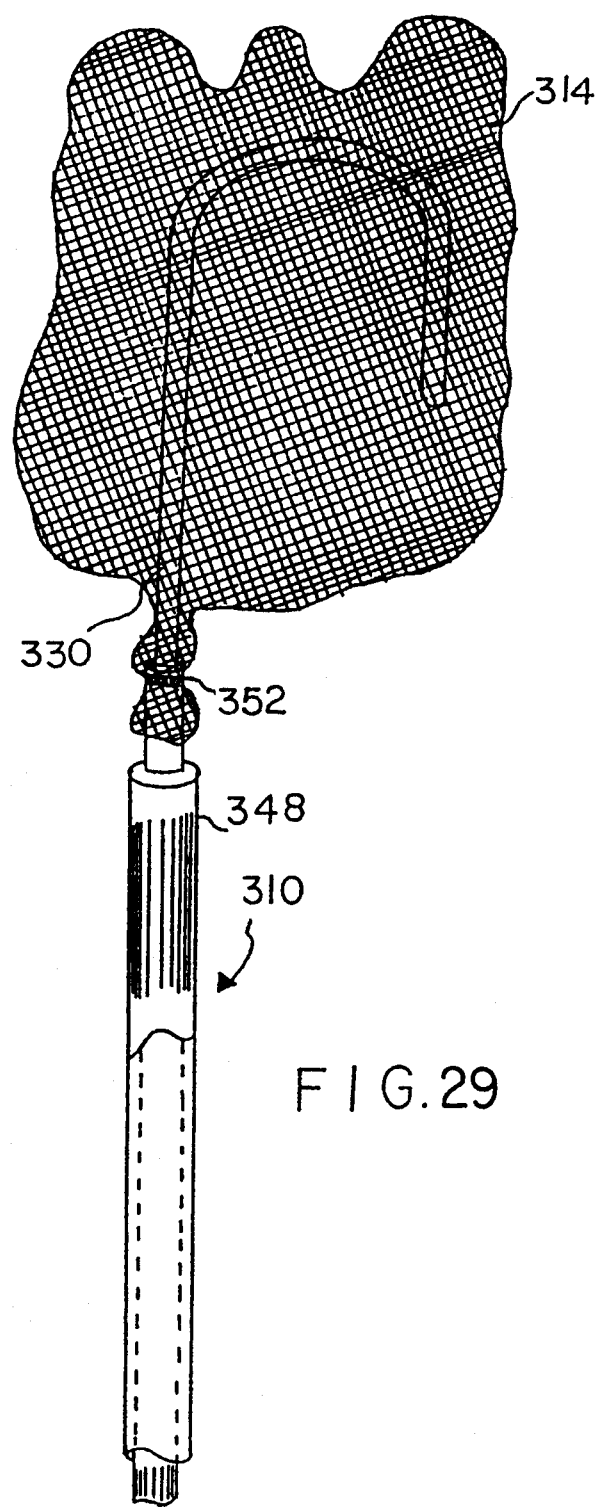
FIG. 29 is a sectional view of a portion of the patch and delivery system which is shown in FIG. 2.
Figure 30:
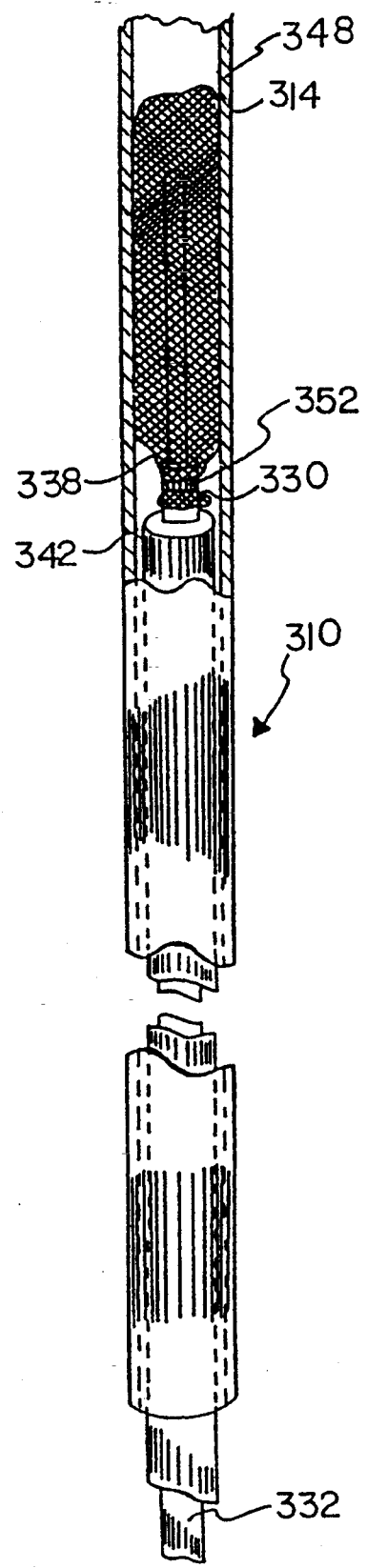
FIG. 30 is a sectional view of the delivery system of FIG. 2 but showing the patch in the sheath prior to deployment.
Figure 31:
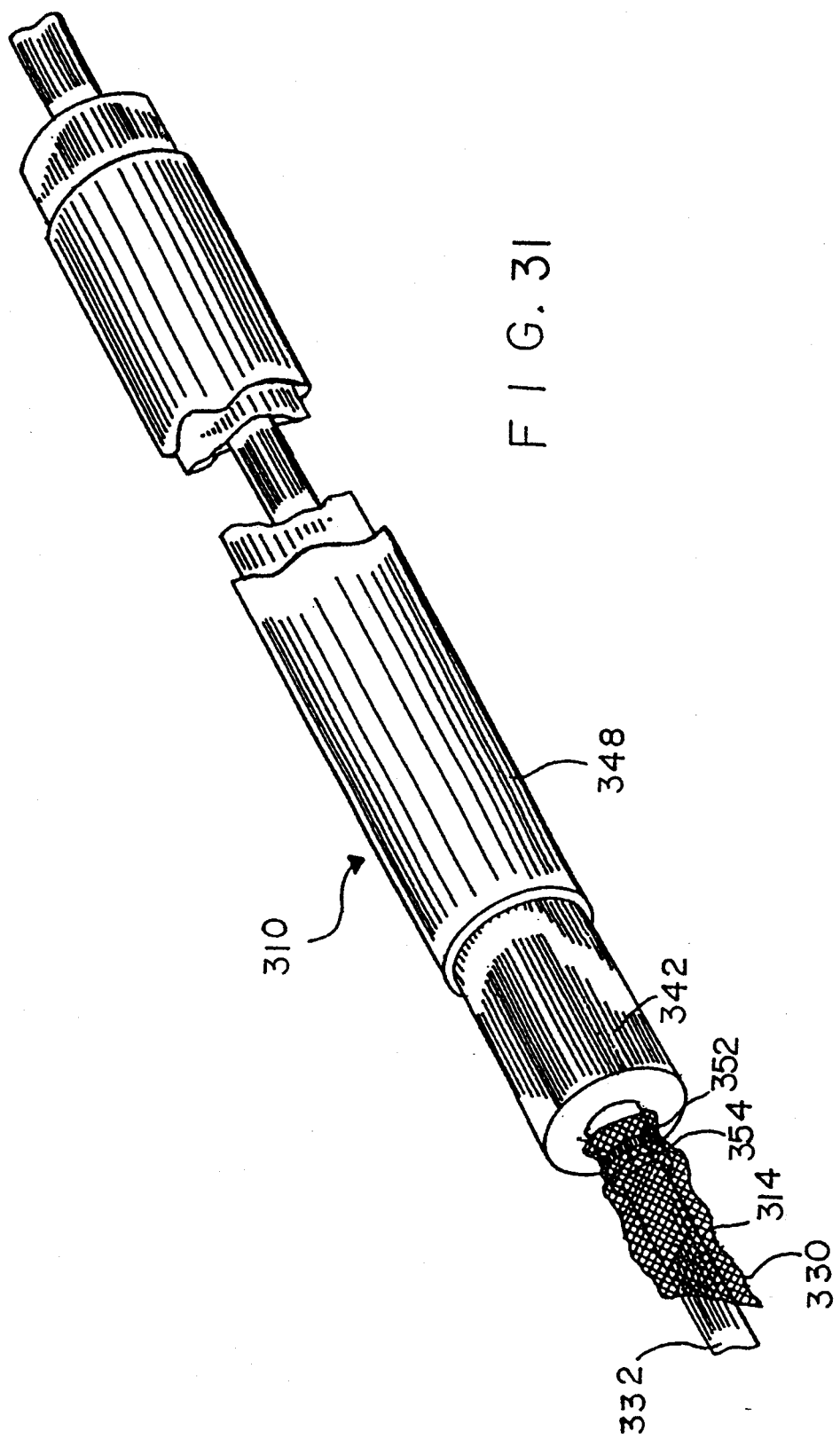
FIG. 31 is a perspective illustration of the patch of the apparatus of the prior Figures and with parts broken away to show certain internal constructions thereof.
Figure 34:
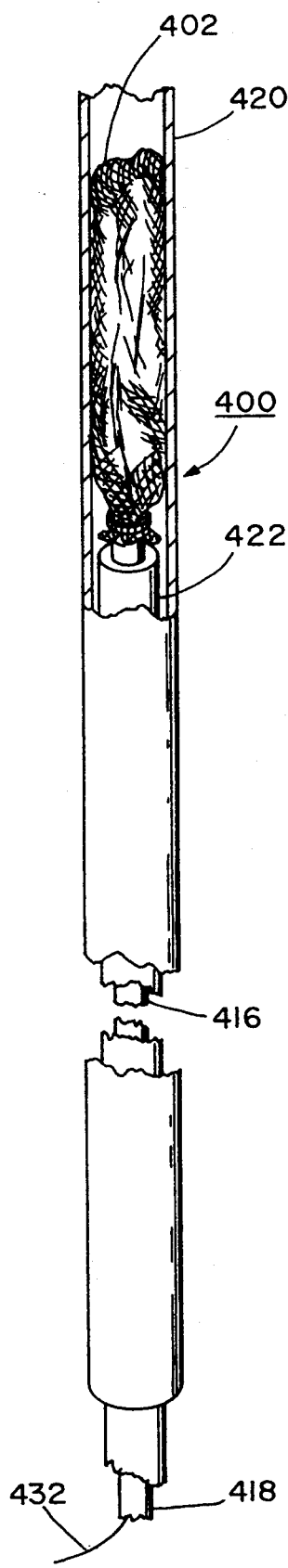
Figure 35:
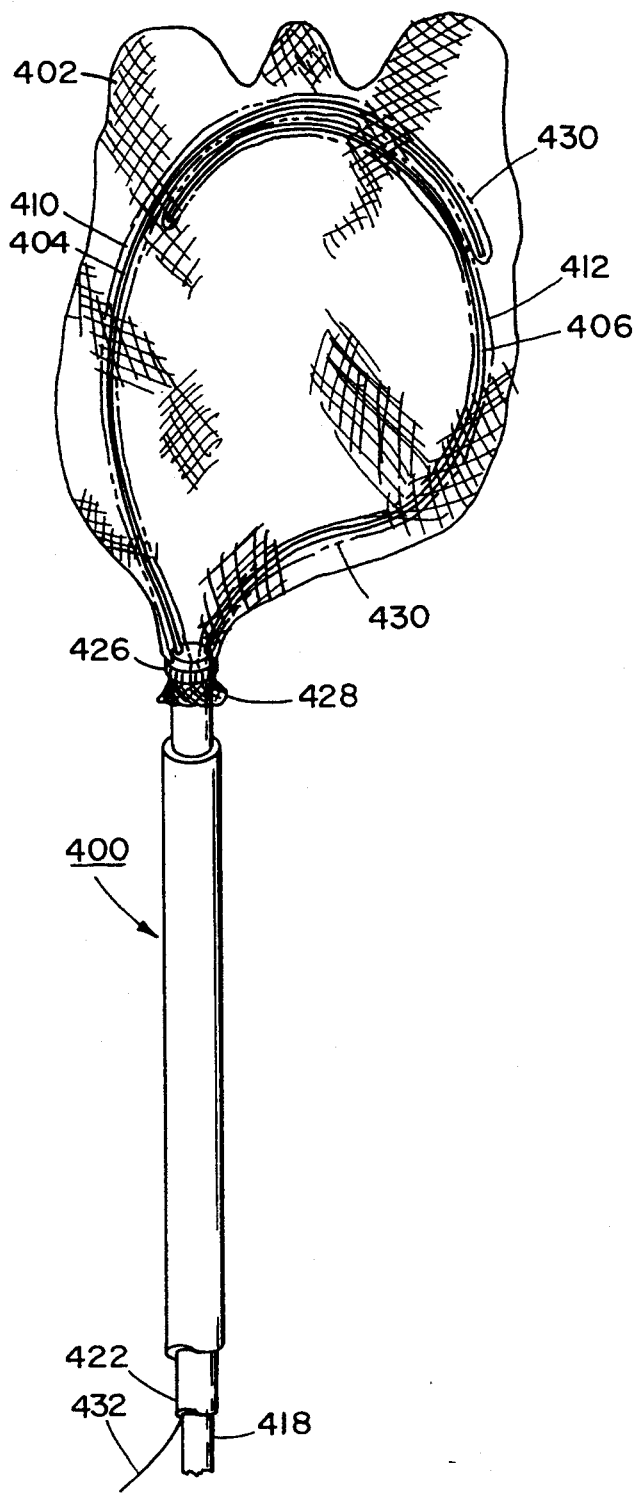

The patch 314 as well as its supporting ribbon 332 and plunger and sheath are preferably prepackaged together as the delivery assembly 310, prior to use by insertion through a sleeve, channel or port which is conventionally placed in a patient by a trochar. The entire delivery assembly 310 is easily seen in FIGS. 29 and 30, sectional views.

In operation and use, the introducer 310, patch, sheath, plunger and ribbon, is inserted through the channel in the patient with its distal end adjacent to the area of the abdominal wall to be patched. The patch 314 are prepositioned with in the sheath 348 as shown in FIG. 4. The introducer 310 then is moved forwardly by the surgeon moving the introducer with respect to the channel. The ribbon, loop and patch move with the introducer when relative movement occurs between the channel and introducer. The plunger is then moved forward from the sheath by either pushing the plunger forwardly with respect to the sheath or withdrawing the sheath with respect to the plunger. With the patch disposed out of the sheath, the ribbon is advanced with respect to the plunger to effect the positioning and orientation of the patch.

The passageway may be formed of a material which is impervious to the flow of fluid (air, water or the like) therethrough. In such embodiment, the expansion of the patch when exterior of the plunger is effected by a flow of air into the passageway of the patch prior to final positioning and attaching of the patch to the area to be repaired. The entire patch could be constructed as a flat balloon or pillow.

Using a second laparoscopic opening, the surgeon will position the edges of the patch into final position. Staples, sutures or clips are employed to secure the patch in its final position. The ribbon is then withdrawn from the passageway into the plunger. Thereafter, the passageway of the patch is detached adjacent to the distal end of the plunger to effect removal of the plunger and ribbon from the patient.

Markings in a grid pattern are preferably formed on the patch to ensure proper positioning and attachment to the patient. Additional markings are also preferably formed on the sleeve and ribbon to indicate the linear and rotational orientation of the sleeve and, hence, the patch. To that extent an axial marking on the sleeve extends proximally from the distal end to a location for indicating the proximal end of the patch. Any one or more or alternate markings could be utilized for these purposes. Such markings could be visually observable.

Shown in FIGS. 32, 33, 34 and 35 are various illustrations of an improved delivery system 400 for a patch 402. In accordance with this embodiment, two ribbons 404 and 406 are employed for supporting the periphery of a patch 402. Each such ribbon is provided with its own passageway 410 and 412. Each passageway receives and guides a separate portion or component of a resilient ribbon. At their distal ends, the ribbons follow a curved path, generally overlapping each other for a portion of their extreme ends. At their proximal end, they are coupled together to a single rod 416 which, at its proximal end 418, may be manipulated by a surgeon to advance the patch 402 to outside of the sheath 420 with or without a separate coaxial plunger 422 to effect patch expansion. After the patch has been secured to a patient by a surgeon, the ribbon components are concurrently withdrawn which will cause the withdrawal of the ribbons from the passageways at the periphery of the patch. The patch is coupled to the introducer by a strap 426. After removal of the ribbon, the distal end 428 of the patch may be detached from the introducer or plunger 422 by the surgeon so that only patch material remains internal of the patient after the operation.

The passageways 410 and 412 are preferably secured to the periphery of the patch 402 by a chain stitch 430. A string 432 extends from the end of the chain stitch, through the plunger, for being pulled by a surgeon. This removes the thread of the stitch and allows separation of passageways from the patch. Thereafter, the passageway may be removed from the patient.

Figures 36, 38:
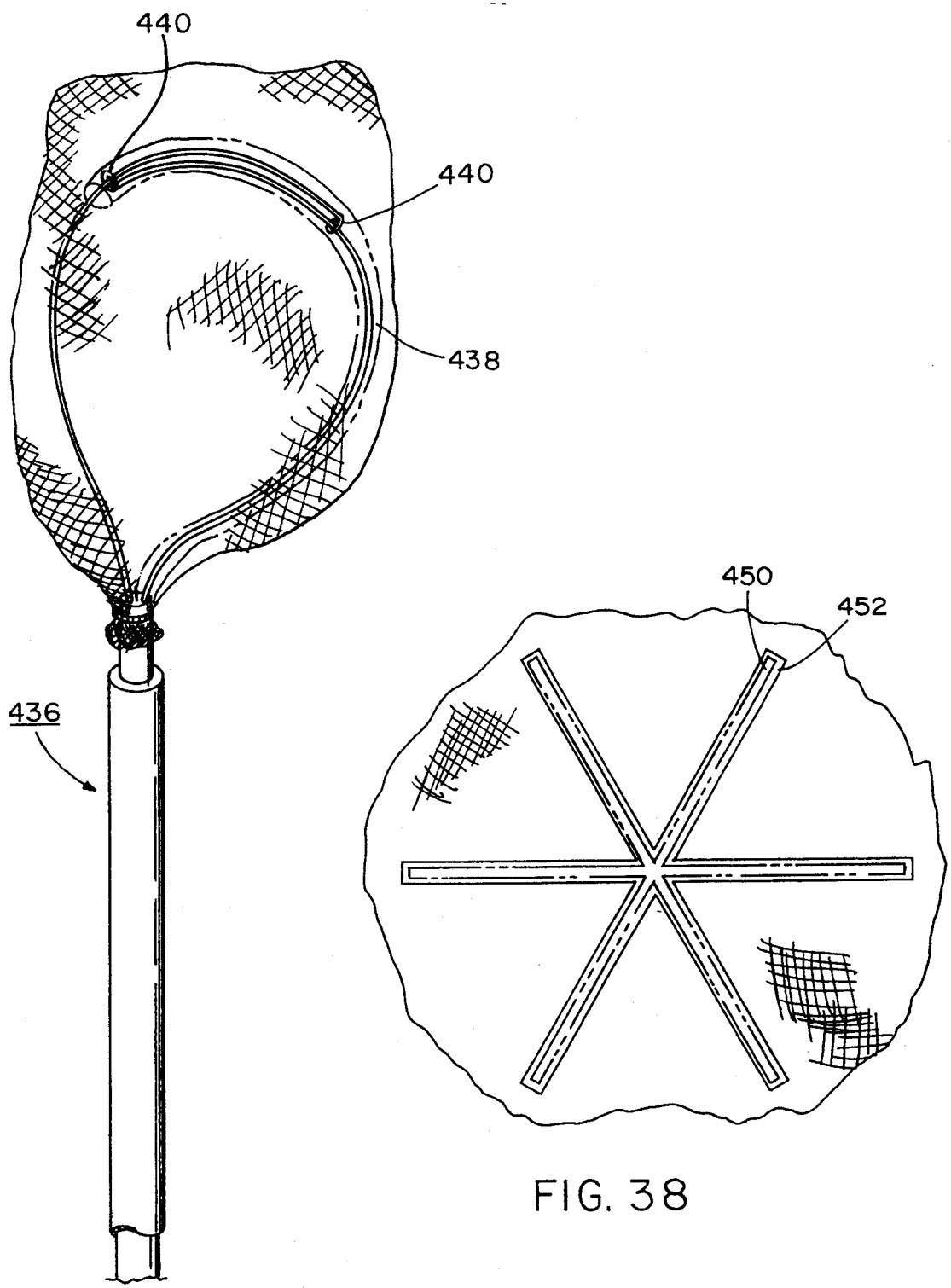
FIG. 36 is an illustration of an additional alternate active patch delivery system.
FIGS. 37 through 43 are seven alternate embodiments of a passive patch.

The FIG. 36 embodiment is a delivery system 436 similar to that of FIGS. 32 through 35 except that only a single passageway 438 is utilized at the periphery of the patch 402. The distal ends of each portion of the ribbons 404 and 406 are provided with a loop 440 for guiding the motion of one portion of the ribbon with respect to the other during expanding and contraction of the ribbon and patch. The loops 440 preclude excessive movement of the ends of the patch and dissociation with respect to each other and with respect to the patch. As depicted in FIG. 36, the distal end of ribbons 404 and 406 each includes a loop 440 of which the other ribbon is threaded therethrough. Both ribbons are positioned in single passageway 438 and are interconnected therein. As a result, the distal end of each ribbon is slidably interconnected to the other ribbon to expand and contract the loop formed by the slidably interconnected ribbons and correspondingly to expand and contract the patch.

FIGS. 37 through 43 represent alternate embodiments of the patch per se. In the FIG. 37 embodiment, a pair of resilient ribbon-like members 442 are formed in a cross-shaped configuration and attached to one surface of the patch 444 as by stitching 446, staples or the like. A hat-shaped cylindrical plug 448 may extend outwardly from the face of the patch. The ribbon-like men, pets in this and the following embodiment are similar to those of the prior embodiments. In the FIG. 38 embodiment, multiple, three rather than two ribbon-like resilient members 450 are utilized. In this embodiment, the ribbon-like members are formed as a single component and are located in sleeves 452 and oriented in a crossing fashion coupled at the midpoint of the patch. In these two embodiments, expansion and contraction of the patch is about a point adjacent to the center and may occur actively as a function of the resilient members.

Figure 37:
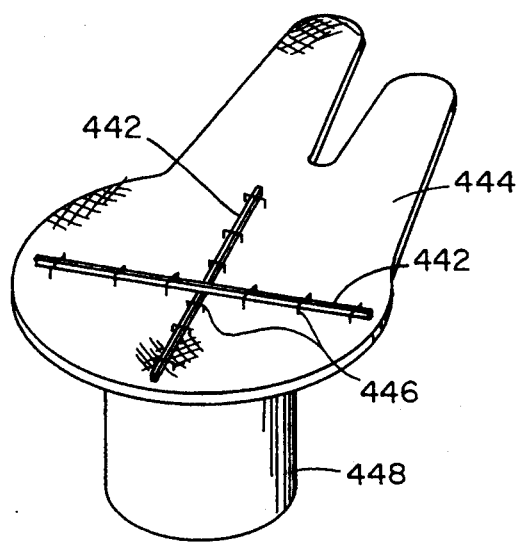
Figure 39:
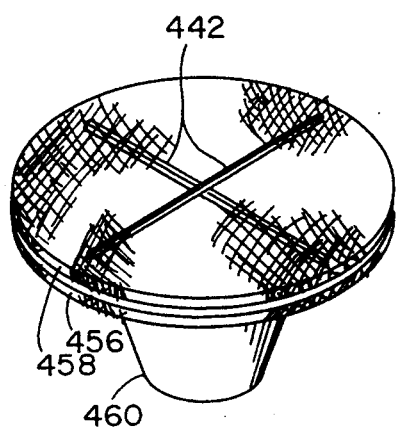
Figure 40:
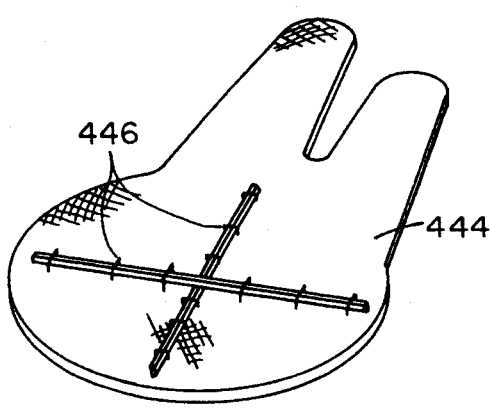

FIG. 39 is similar to FIG. 37 except that the resilient members 44 are held in position by being sandwiched between a pair of similarly shaped patches 456 and 458. Further, the plug 460 is shaped in a frustro-conical configuration. FIG. 40 is also similar to FIG. 37 except that no plug is utilized.

Figure 41:
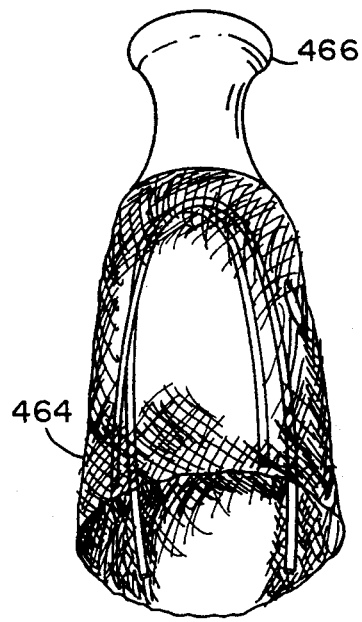
Figure 42:
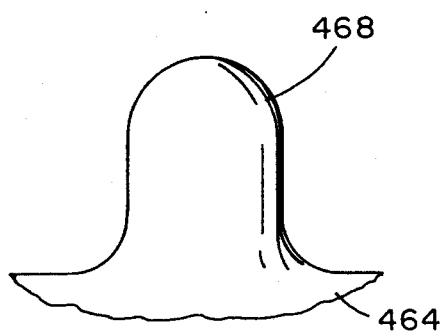
Figure 43:
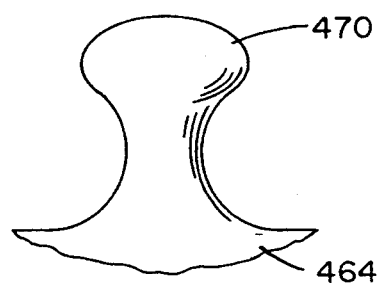

Various plugs are shown in FIGS. 41 through 47. The FIG. 41 showing illustrates a patch 464 constrained for positioning within a sheath. The plug 466 has a nipple-shaped configuration. FIGS. 42 and 43 show patches 464 with plugs 468 and 470 of curved and nipple shapes, the nipple featuring an enlarged end for swelling when irrigated for greater retention in an opening of the patient.

Figure 44:
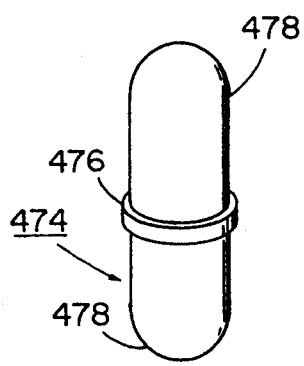
FIGS. 44 through 47 are two additional embodiments of a plug.
Figure 45:
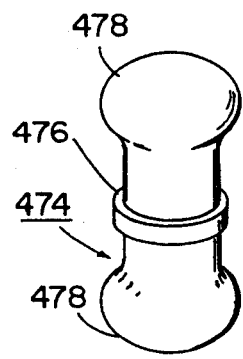

FIGS. 44 and 45 illustrate a plug 474 shaped generally cylindrically but with a strap 476 at the center to preclude swelling when irrigated. Irrigation thus allows the ends 478 of the plug to swell for maintaining its original position. Central swelling is precluded by the strap. Note the post irrigation configuration of FIG. 45.

Figure 46:
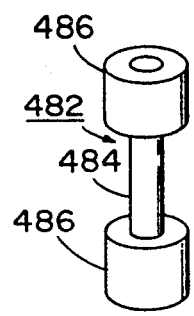
Figure 47:
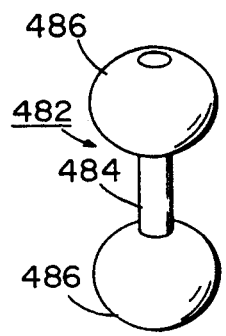
Figure 48:
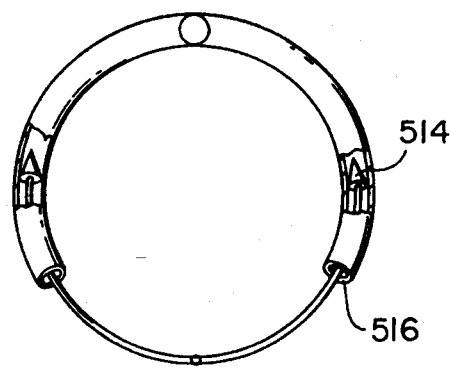
FIGS. 48 through 55 are seven alternate embodiments of a patch.
Figure 49:
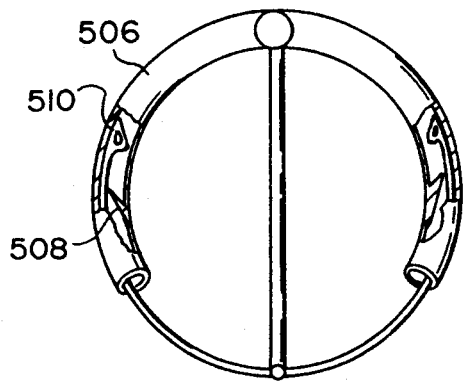

FIGS. 46 and 47 show a plug 482, again in a dumbbell configuration. A central shaft 484 is of an elastomeric material which will not swell when irrigated. The ends 486 are of a material, known in the arts, so that after irrigation, the ends swell to the FIG. 47 shape to function as in the FIG. 45 embodiment.

FIGS. 48 through 55 show even further embodiments of the patch. In these embodiments, the expanding of the patch within the patient is done in a planar path of movement about a line through the center of the patch. In the prior embodiments of FIGS. 37 through 43, the spreading of the patch occurred about a central point on the patch. In the FIG. 52 embodiment, stitches 490 hold a central rod 492 and adjacent side members 494 adjacent to the periphery of the patch 496. The resilience of the ribbon-like side members 494 allows contraction and expansion of the patch 496 about the central axis through the central rod 492.

Figure 52:
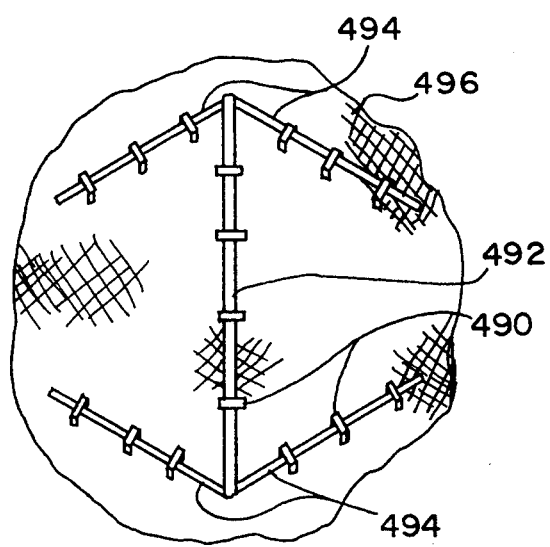
Figure 53:
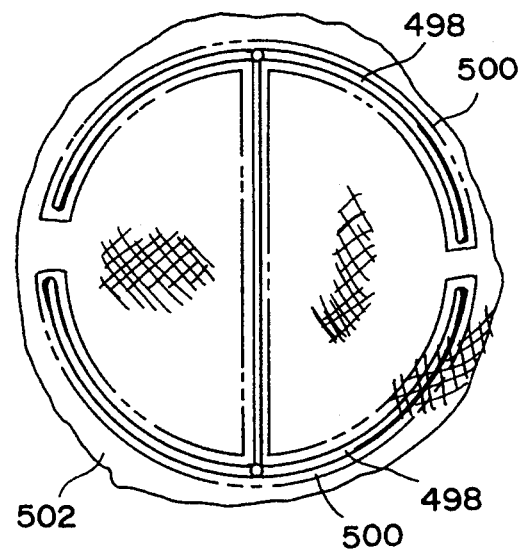
Figure 54:
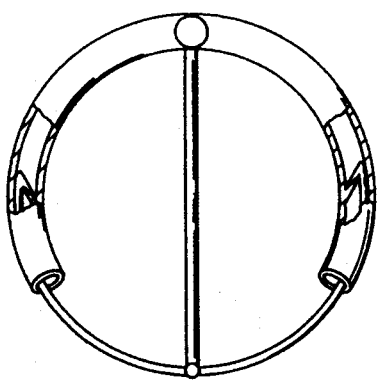

The FIG. 53 embodiment is the same as FIG. 52 except that the side members 498 are not stitched but rather held in position by tubes 500 secured to the fabric of the mesh patch 502. In the FIG. 53 embodiment, the side members 498 are curved to parallel the periphery.

The FIG. 48–55 embodiments are similar to the embodiment of FIGS. 52 and 53. These embodiments, however, preclude the ends of the side men%bets from becoming separated. This is effected in FIGS. 48 and 49 by having the side members at one end formed as flexible tubes 506 with restraining projections 508 adjacent to the ends. The other member has ends formed with barbs 510 which function with the projections 508 for precluding separation of the ends of the side members within the patient. The barbs face inwardly to preclude movement outwardly thereof. Sharp ends are thus precluded from movement of the plane of the patch for patient safety. In the FIG. 48 embodiment, the ends of side members are formed with cone-like barbs 514, positioned through diaphragms 516 in the ends of the tubes to allow movement to the FIG. 48 orientation but to preclude separation. Note is taken that the FIG. 48 embodiment eliminates the central bar.

Figure 50:
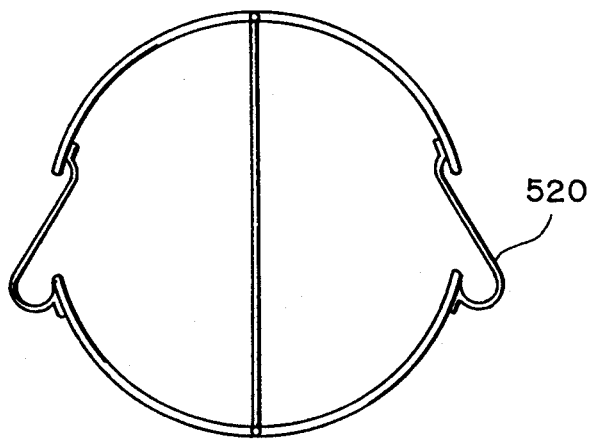

The embodiment of FIG. 50, includes flexible tethers 520, such as strings, holding the ends of the side pieces as by plastic welding, an adhesive, a free end frictional coupled in a tube, or the like. This again is done to preclude excessive separation thereof.

Figure 51:
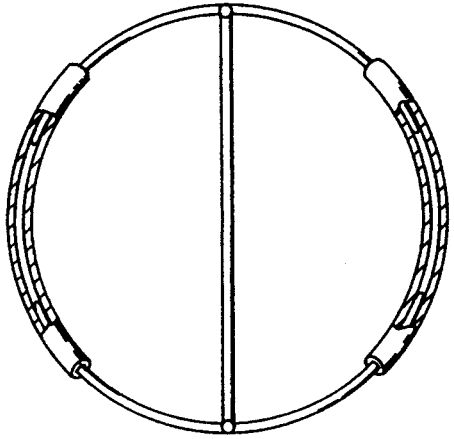
Figure 55:
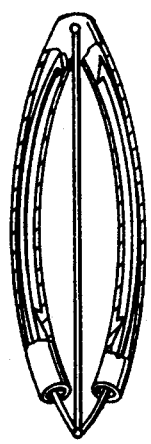

The FIG. 51 embodiment is similar to FIG. 53 except that flexible tubes 524 receive the free ends of all the side members. FIG. 55 simply illustrates the closed orientation within a sheath for any of the embodiments of FIGS. 48 through 54.

Figure 56:
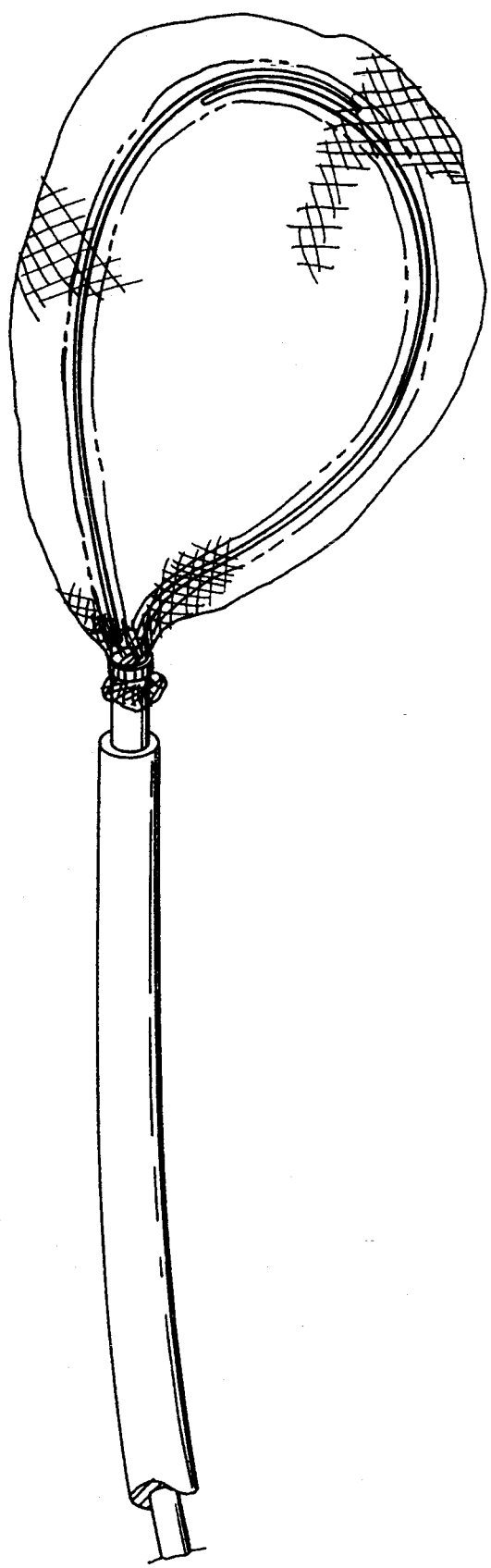
FIG. 56 is an alternate embodiment of the delivery apparatus.

Lastly, FIG. 56 illustrates a curved assembly. The curve may be attained by simply using a flexible sheath, plunger and rod. In the alternative, the central rod may be flexible while the sheath and plunger are articulated, moveable to any curve, in a conventional manner. Conversely, the central rod may be articulated while the sheath and plunger would be flexible.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,
What is claimed is:

1. Apparatus for laparoscopically patching hernias comprising:
    a tubular sheath having a distal end and a proximal end;
    a tubular plunger located within and moveable with respect to the sheath, the tubular plunger having a proximal end and a distal end with the proximal end of the tubular plunger extending proximally outwardly of the sheath for manipulation by a surgeon;
    elongated means having a proximal end and a bifurcated distal end adapted to form a loop, the proximal end of the elongated means extending proximally outwardly of the sheath for manipulation by a surgeon; and
    a patch supported on the loop for movement therewith, the patch having passageway means for receipt of the loop to retain the patch in a planar configuration.

2. The apparatus as set forth in claim 1 wherein the passageway means includes two separate passageways, one for each component of the bifurcated distal end of the elongated means.

3. The apparatus as set forth in claim 1 wherein the passageway means includes a single passageway for first and second components of the bifurcated distal end of the elongated means.

4. The apparatus as set forth in claim 1 wherein the passageway means is coupled to the patch with a chain stitch with a string extending therefrom, through the tubular plunger and exterior of the patient for being pulled by a surgeon to separate the passageway means from the patch.

5. The apparatus as set forth in claim 1 wherein at least one of the tubular sheath and tubular plunger is articulated for effecting curved movement of the elongated means.

6. The apparatus as set forth in claim 1 wherein the elongated means is articulated and the sheath and plunger are flexible.

7. The apparatus as set forth in claim 1 wherein the tubular sheath and plunger are curved.

8. The apparatus as set forth in claim 1 wherein the passageway means includes a single passageway, extending from a distal end of the patch for the receipt of the bifurcated distal end of the elongated means.

9. The apparatus as set forth in claim 23 wherein the elongated means are supported between an upper patch component and a lower patch component in a sandwiched configuration.

10. Apparatus for use by a surgeon to repair a weakened, deranged portion of the anatomy of a patient comprising:
    a sheath having a distal end positionable within a patient and a proximal end positioned exterior of the patient for manipulation by a surgeon, the sheath being of a length to extend from exterior of a patient through a laparoscopic opening into a surgical cavity of the patient;
    a prosthesis formed of flexible, essentially inextensible material moveable from interior of the sheath to a location adjacent to the deranged portion to be repaired;
    resilient means extending along and attached to a periphery of the prosthesis to effect its opening into a generally planar configuration upon removal from the sheath; and
    an introducer positioned within the sheath and having a distal end coupled to the prosthesis, the introducer adapted to effect movement of the prosthesis from interior of the sheath to exterior thereof.

11. The apparatus as set forth in claim 10 wherein the prosthesis has a generally square configuration.

12. The apparatus as set forth in claim 10 wherein the resilient means is in a generally I-shaped configuration with a central bar and side members extending from ends thereof along the periphery of the prosthesis for folding the prosthesis in a plane about the central bar.

13. The apparatus as set forth in claim 12 wherein the side members are straight.

14. The apparatus as set forth in claim 12 wherein the side members are curved.

15. The apparatus as set forth in claim 14 wherein the side members include tubular members and nontubular members adapted to be received into said tubular members.

16. The apparatus as set forth in claim 13 and further including means to constrain the ends of the side members together.

17. The apparatus as set forth in claim 16 wherein the means to constrain are two-dimensional barbs at the ends of the side members and hooks formed in the tubular members.

18. The apparatus as set forth in claim 16 wherein the means to constrain includes three-dimensional barbs received in a diaphragm of the tubular members to preclude separation therebetween.

19. The apparatus as set forth in claim 17 wherein the means to constrain are tethers.

20. The apparatus as set forth in claim 10 wherein the resilient means are curved members along the periphery of the prosthesis detached from each other.

21. A method for the laparoscopic repair of abdominal hernias by a surgeon through the patching of weakened portions of the abdominal part to be repaired comprising the steps of:
    providing a patch formed of flexible, inextensible material and positionable in a plane adjacent to the weakened portions of the abdominal part to be repaired, the patch having elongated passageway means located in the plane of the patch and extending along a periphery of the patch;
    providing an elongated interior ribbon having a bifurcated distal end positioned within the passageway means and slidable within the passageway means, the ribbon being sufficiently rigid whereby it may be remotely pushed into the passageway;

providing an elongated intermediate cylindrical plunger having an interior slidably receiving the ribbon, the plunger having a distal end coupled to the patch and a proximal end to be manipulated by the surgeon;

providing an elongated exterior cylindrical sheath having an interior slidably receiving the plunger, the ribbon and the patch, the sheath having a distal end adjacent to the patch and a proximal end to be manipulated by the surgeon, the sheath being of a length to extend from exterior of a patient through a laparoscopic port into a surgical cavity which includes the part to be repaired;

positioning the patch and the distal ends of the ribbon, plunger and sheath into a patient adjacent to the area to be repaired;

advancing the patch and plunger from the sheath;

advancing the ribbon within the passageway of the patch to expand the patch;

coupling the patch to the area to be repaired;

withdrawing the ribbon from the patch;

separating the patch from the plunger; and withdrawing the ribbon, plunger and sheath from the patient.

* * * * *